(12) United States Patent
Bava

(10) Patent No.: US 12,076,701 B2
(45) Date of Patent: Sep. 3, 2024

(54) CAPTURING OLIGONUCLEOTIDES IN SPATIAL TRANSCRIPTOMICS

(71) Applicant: 10X Genomics, Inc., Pleasanton, CA (US)

(72) Inventor: Felice Alessio Bava, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 648 days.

(21) Appl. No.: 17/161,007

(22) Filed: Jan. 28, 2021

(65) Prior Publication Data

US 2021/0237022 A1 Aug. 5, 2021

Related U.S. Application Data

(60) Provisional application No. 62/985,281, filed on Mar. 4, 2020, provisional application No. 62/968,312, filed on Jan. 31, 2020.

(51) Int. Cl.
*B01J 19/00* (2006.01)

(52) U.S. Cl.
CPC .. *B01J 19/0046* (2013.01); *B01J 2219/00608* (2013.01); *B01J 2219/00722* (2013.01)

(58) Field of Classification Search
CPC ........ B01J 19/0046; B01J 2219/00608; C12Q 1/6841; C12Q 2525/161; C12Q 2525/173; C12Q 2525/313; C12Q 2527/107
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 4,988,617 A | 1/1991 | Landegren et al. |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,472,881 A | 12/1995 | Beebe et al. |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

Bibikova et al., "Quantitative gene expression profiling in formalin-fixed paraffin-embedded tissues using universal bead arrays," The American Journal of Pathology, Nov. 1, 2004, 165(5):1799- 1807.

(Continued)

*Primary Examiner* — Joseph G. Dauner
(74) *Attorney, Agent, or Firm* — Fish & Richardson P.C.

(57) ABSTRACT

Disclosed are extended and/or branched oligonucleotide capture probe assemblies for use in spatial transcriptomics systems, and methods for making the capture probe assemblies.

16 Claims, 8 Drawing Sheets

(56) References Cited

U.S. PATENT DOCUMENTS

| | | |
|---|---|---|
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,610,287 A | 3/1997 | Nikiforov et al. |
| 5,641,658 A | 6/1997 | Adams |
| 5,648,245 A | 7/1997 | Fire et al. |
| 5,658,751 A | 8/1997 | Yue |
| 5,695,940 A | 12/1997 | Drmanac et al. |
| 5,750,341 A | 5/1998 | Macevicz |
| 5,763,175 A | 6/1998 | Brenner |
| 5,807,522 A | 9/1998 | Brown et al. |
| 5,830,711 A | 11/1998 | Barany et al. |
| 5,837,832 A | 11/1998 | Chee et al. |
| 5,837,860 A | 11/1998 | Anderson et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,919,626 A | 7/1999 | Shi et al. |
| 5,925,545 A | 7/1999 | Reznikoff et al. |
| 5,928,906 A | 7/1999 | Koester et al. |
| 5,958,775 A | 9/1999 | Wickstrrom |
| 5,965,443 A | 10/1999 | Reznikoff et al. |
| 6,013,440 A | 1/2000 | Lipshutz |
| 6,027,889 A | 2/2000 | Barany et al. |
| 6,054,274 A | 4/2000 | Sampson et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,172,218 B1 | 1/2001 | Brenner |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,309,824 B1 | 10/2001 | Drmanac |
| 6,323,009 B1 | 11/2001 | Lasken et al. |
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,391,937 B1 | 5/2002 | Beuhler et al. |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,699,710 B1 | 3/2004 | Kononen |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,259,258 B2 | 8/2007 | Kozlov et al. |
| 7,282,328 B2 | 10/2007 | Kong et al. |
| 7,297,518 B2 | 11/2007 | Quake |
| 7,315,019 B2 | 1/2008 | Turner |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,427,678 B2 | 9/2008 | Pieken et al. |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,492 B2 | 10/2009 | Fu et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,754,429 B2 | 7/2010 | Rigatti |
| 7,776,547 B2 | 8/2010 | Roth |
| 7,776,567 B2 | 8/2010 | Mao |
| 7,803,943 B2 | 9/2010 | Mao |
| 7,844,940 B2 | 11/2010 | Shin et al. |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 7,960,120 B2 | 6/2011 | Rigatti |
| 7,985,565 B2 | 7/2011 | Mayer et al. |
| 8,003,354 B2 | 8/2011 | Shen et al. |
| 8,030,477 B2 | 10/2011 | Cerrina et al. |
| 8,076,063 B2 | 12/2011 | Fan |
| 8,092,784 B2 | 1/2012 | Mao |
| 8,148,068 B2 | 4/2012 | Brenner |
| 8,198,028 B2 | 6/2012 | Rigatti et al. |
| 8,206,917 B2 | 6/2012 | Chee |
| 8,268,554 B2 | 9/2012 | Schallmeiner |
| 8,288,103 B2 | 10/2012 | Oliphant |
| 8,288,122 B2 | 10/2012 | O'Leary et al. |
| 8,383,338 B2 | 2/2013 | Kitzman |
| 8,431,691 B2 | 4/2013 | McKernan et al. |
| 8,460,865 B2 | 6/2013 | Chee |
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,486,625 B2 | 7/2013 | Gunderson |
| 8,507,204 B2 | 8/2013 | Pierce et al. |
| 8,519,115 B2 | 8/2013 | Webster et al. |

(56) References Cited

U.S. PATENT DOCUMENTS

| | | |
|---|---|---|
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,778,849 B2 | 7/2014 | Bowen |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,895,249 B2 | 11/2014 | Shen |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,085,798 B2 | 7/2015 | Chee |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Van Eijk |
| 9,694,361 B2 | 7/2017 | Bharadwaj |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,889,422 B2 | 2/2018 | Smith et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,035,992 B2 | 7/2018 | Gloeckner et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,138,509 B2 | 11/2018 | Church et al. |
| 10,144,966 B2 | 12/2018 | Cantor |
| 10,179,932 B2 | 1/2019 | Church |
| 10,208,982 B2 | 2/2019 | Bannish et al. |
| 10,227,639 B2 | 3/2019 | Levner et al. |
| 10,273,541 B2 | 4/2019 | Hindson et al. |
| 10,308,982 B2 | 6/2019 | Chee |
| 10,357,771 B2 | 7/2019 | Bharadwaj |
| 10,370,698 B2 | 8/2019 | Nolan et al. |
| 10,415,080 B2 | 9/2019 | Dunaway et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,008,607 B2 | 5/2021 | Chee |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,479,809 B2 | 10/2022 | Frisen et al. |
| 11,479,810 B1 | 10/2022 | Chee |

(56) References Cited

U.S. PATENT DOCUMENTS

| | | |
|---|---|---|
| 11,492,612 B1 | 11/2022 | Dadhwal |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |
| 11,702,693 B2 | 7/2023 | Bharadwaj |
| 11,702,698 B2 | 7/2023 | Stoeckius |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 11,761,030 B2 | 9/2023 | Chee |
| 11,761,038 B1 | 9/2023 | Stoeckius |
| 11,767,550 B2 | 9/2023 | Chee |
| 11,768,175 B1 | 9/2023 | Kim et al. |
| 11,773,433 B2 | 10/2023 | Gallant et al. |
| 11,781,130 B2 | 10/2023 | Dadhwal |
| 11,788,122 B2 | 10/2023 | Frisen et al. |
| 11,795,498 B2 | 10/2023 | Frisen et al. |
| 11,795,507 B2 | 10/2023 | Chell et al. |
| 11,808,769 B2 | 11/2023 | Uytingco et al. |
| 11,821,024 B2 | 11/2023 | Chee et al. |
| 11,821,035 B1 | 11/2023 | Bent et al. |
| 11,827,935 B1 | 11/2023 | Ramachandran Iyer et al. |
| 11,835,462 B2 | 12/2023 | Bava |
| 11,840,687 B2 | 12/2023 | Gallant et al. |
| 11,840,724 B2 | 12/2023 | Chew et al. |
| 11,845,979 B2 | 12/2023 | Engblom et al. |
| 11,859,178 B2 | 1/2024 | Gallant et al. |
| 11,866,767 B2 | 1/2024 | Uytingco et al. |
| 11,866,770 B2 | 1/2024 | Chee |
| 11,873,482 B2 | 1/2024 | Kim et al. |
| 11,891,654 B2 | 2/2024 | Alvarado Martinez et al. |
| 11,898,205 B2 | 2/2024 | Bava |
| 2001/0055764 A1 | 12/2001 | Empendocles et al. |
| 2002/0040275 A1 | 4/2002 | Cravatt |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0137031 A1 | 9/2002 | Wolber |
| 2002/0164611 A1 | 11/2002 | Bamdad |
| 2002/0168645 A1 | 11/2002 | Taylor |
| 2003/0017451 A1 | 1/2003 | Wang et al. |
| 2003/0022207 A1 | 1/2003 | Balasubramanian |
| 2003/0040035 A1 | 2/2003 | Slamon |
| 2003/0064398 A1 | 4/2003 | Barnes |
| 2003/0073086 A1 | 4/2003 | Guire et al. |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0211489 A1 | 11/2003 | Shen et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0224326 A1 | 11/2004 | Kim et al. |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064432 A1 | 3/2005 | Huang et al. |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0130173 A1 | 6/2005 | Leamon et al. |
| 2005/0130188 A1 | 6/2005 | Walt |
| 2005/0136414 A1 | 6/2005 | Gunderson et al. |
| 2005/0164292 A1 | 7/2005 | Farooqui |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0239119 A1 | 10/2005 | Tsukada et al. |
| 2005/0244850 A1 | 11/2005 | Huang |
| 2005/0260653 A1 | 11/2005 | LaBaer |
| 2005/0266417 A1 | 12/2005 | Barany et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0188901 A1 | 8/2006 | Barnes et al. |
| 2006/0199183 A1 | 9/2006 | Valat et al. |
| 2006/0199207 A1 | 9/2006 | Matysiak |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0275799 A1 | 12/2006 | Banerjee et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0231823 A1 | 10/2007 | McKernan |
| 2007/0254305 A1 | 11/2007 | Paik et al. |
| 2007/0264656 A1 | 11/2007 | Kawamura |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0032301 A1 | 2/2008 | Rank et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |

(56) References Cited

U.S. PATENT DOCUMENTS

| | | |
|---|---|---|
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0062148 A1 | 3/2009 | Goldberg |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0253581 A1 | 10/2009 | van Eijk et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2010/0009871 A1 | 1/2010 | Reed et al. |
| 2010/0035249 A1 | 2/2010 | Hayashizaki et al. |
| 2010/0055733 A1 | 3/2010 | Lutolf et al. |
| 2010/0069263 A1 | 3/2010 | Shendure et al. |
| 2010/0105052 A1 | 4/2010 | Drmanac et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0151464 A1 | 6/2010 | Stuelpnagel et al. |
| 2010/0173384 A1 | 7/2010 | Johnsson et al. |
| 2010/0184614 A1 | 7/2010 | Ye et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0059865 A1 | 3/2011 | Smith et al. |
| 2011/0111409 A1 | 5/2011 | Sinicropi et al. |
| 2011/0152111 A1 | 6/2011 | Fan et al. |
| 2011/0245101 A1 | 10/2011 | Chee et al. |
| 2011/0245111 A1 | 10/2011 | Chee |
| 2011/0275077 A1 | 11/2011 | James |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0129248 A1 | 5/2012 | Chee et al. |
| 2012/0135871 A1 | 5/2012 | van Eijk et al. |
| 2012/0156728 A1 | 6/2012 | Li et al. |
| 2012/0157322 A1 | 6/2012 | Myllykangas |
| 2012/0202698 A1 | 8/2012 | Van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0270748 A1 | 10/2012 | Chee et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0023433 A1* | 1/2013 | Luo ............... C12Q 1/6841 436/501 |
| 2013/0035239 A1 | 2/2013 | Kong et al. |
| 2013/0065768 A1 | 3/2013 | Zheng et al. |
| 2013/0065788 A1 | 3/2013 | Glezer et al. |
| 2013/0079232 A1 | 3/2013 | Kain et al. |
| 2013/0096033 A1 | 4/2013 | Routenberg |
| 2013/0109595 A1 | 5/2013 | Routenberg |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0243224 A1 | 8/2014 | Barnard et al. |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2014/0378345 A1 | 12/2014 | Hindson et al. |
| 2014/0378350 A1 | 12/2014 | Hindson et al. |
| 2015/0000854 A1 | 1/2015 | Gann-Fetter et al. |
| 2015/0005447 A1 | 1/2015 | Berti et al. |
| 2015/0087027 A1 | 3/2015 | Makarov et al. |
| 2015/0246336 A1 | 9/2015 | Somoza et al. |
| 2015/0292988 A1 | 10/2015 | Bharadwaj et al. |
| 2015/0344942 A1 | 12/2015 | Frisen et al. |
| 2015/0376609 A1 | 12/2015 | Hindson et al. |
| 2016/0019337 A1 | 1/2016 | Roberts et al. |
| 2016/0024576 A1 | 1/2016 | Chee |
| 2016/0041159 A1 | 2/2016 | Labaer et al. |
| 2016/0060687 A1 | 3/2016 | Zhu et al. |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0201125 A1* | 7/2016 | Samuels ............... G01N 33/53 506/4 |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0283860 A1 | 4/2017 | Kool et al. |
| 2017/0159109 A1 | 6/2017 | Zheng et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0335297 A1 | 11/2017 | Ha et al. |
| 2017/0335410 A1 | 11/2017 | Driscoll et al. |
| 2017/0342405 A1 | 11/2017 | Fu et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0080019 A1 | 3/2018 | Blainey et al. |
| 2018/0094316 A1 | 4/2018 | Oliphant et al. |
| 2018/0112261 A1 | 4/2018 | Van Driel et al. |
| 2018/0127817 A1 | 5/2018 | Borchert et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0291427 A1 | 10/2018 | Edelman |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2019/0017106 A1 | 1/2019 | Frisen et al. |
| 2019/0024153 A1 | 1/2019 | Frisen et al. |
| 2019/0024154 A1 | 1/2019 | Frisen et al. |
| 2019/0032121 A1 | 1/2019 | Daugharthy |

(56) References Cited

U.S. PATENT DOCUMENTS

| | | |
|---|---|---|
| 2019/0055594 A1 | 2/2019 | Samusik et al. |
| 2019/0064173 A1 | 2/2019 | Bharadwaj et al. |
| 2019/0071656 A1 | 3/2019 | Chang et al. |
| 2019/0085383 A1 | 3/2019 | Church et al. |
| 2019/0119735 A1 | 4/2019 | Deisseroth et al. |
| 2019/0135774 A1 | 5/2019 | Orbai |
| 2019/0144936 A1 | 5/2019 | Gierahn et al. |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0360034 A1 | 11/2019 | Zhou et al. |
| 2019/0360043 A1 | 11/2019 | Pham et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0173985 A1 | 6/2020 | Dong et al. |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0140982 A1 | 5/2021 | Uytingco et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |

(56) References Cited

U.S. PATENT DOCUMENTS

| | | |
|---|---|---|
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0416807 A1 | 1/2023 | Chee |
| 2023/0416808 A1 | 1/2023 | Sukovich et al. |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |
| 2023/0295722 A1 | 9/2023 | Bharadwaj |
| 2023/0304074 A1 | 9/2023 | Chee et al. |
| 2023/0304078 A1 | 9/2023 | Frisen et al. |
| 2023/0313279 A1 | 10/2023 | Giacomello et al. |
| 2023/0323340 A1 | 10/2023 | Dadhwal |
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |
| 2023/0358733 A1 | 11/2023 | Chee |
| 2023/0366008 A1 | 11/2023 | Chew et al. |
| 2023/0383285 A1 | 11/2023 | Kim et al. |
| 2023/0383344 A1 | 11/2023 | Stoeckius |
| 2023/0392204 A1 | 12/2023 | Chell et al. |
| 2023/0393071 A1 | 12/2023 | Bava |
| 2023/0407404 A1 | 12/2023 | Baumgartner et al. |
| 2023/0416850 A1 | 12/2023 | Singh et al. |
| 2024/0002931 A1 | 1/2024 | Bava |
| 2024/0011081 A1 | 1/2024 | Chee |
| 2024/0011090 A1 | 1/2024 | Chew et al. |
| 2024/0018572 A1 | 1/2024 | Mignardi |
| 2024/0018575 A1 | 1/2024 | Gallant et al. |
| 2024/0018589 A1 | 1/2024 | Schnall-Levin et al. |
| 2024/0026445 A1 | 1/2024 | Ramachandran Iyer et al. |
| 2024/0035937 A1 | 2/2024 | Cox et al. |
| 2024/0043908 A1 | 2/2024 | Chew et al. |
| 2024/0043925 A1 | 2/2024 | Bent et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 107849606 | 3/2018 |
| CN | 108949924 | 12/2018 |
| EP | 1782737 | 5/2007 |
| EP | 1910562 | 4/2008 |
| EP | 1923471 | 5/2008 |
| EP | 1929039 | 6/2008 |
| EP | 2002017 | 12/2008 |
| EP | 2292788 | 3/2011 |
| EP | 2302070 | 3/2011 |
| EP | 2580351 | 4/2013 |
| EP | 2881465 | 6/2015 |
| EP | 3013984 | 5/2016 |
| EP | 3511423 | 7/2019 |
| EP | 3541956 | 9/2019 |
| EP | 3425053 | 8/2020 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 1999/044062 | 9/1999 |
| WO | WO 1999/044063 | 9/1999 |
| WO | WO 1999/067641 | 12/1999 |
| WO | WO 2000/017390 | 3/2000 |
| WO | WO 2000/063437 | 10/2000 |
| WO | WO 2001/006012 | 1/2001 |
| WO | WO 2001/007915 | 2/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |

(56) References Cited

FOREIGN PATENT DOCUMENTS

| | | |
|---|---|---|
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/065814 | 7/2005 |
| WO | WO 2005/113804 | 12/2005 |
| WO | WO 2006/020515 | 2/2006 |
| WO | WO 2006/124771 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/022332 | 2/2008 |
| WO | WO 2008/069906 | 6/2008 |
| WO | WO 2008/093098 | 8/2008 |
| WO | WO 2009/032167 | 3/2009 |
| WO | WO 2009/036525 | 3/2009 |
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2010/127186 | 11/2010 |
| WO | WO 2011/008502 | 1/2011 |
| WO | WO 2011/014879 | 2/2011 |
| WO | WO 2011/062933 | 5/2011 |
| WO | WO 2011/068088 | 6/2011 |
| WO | WO 2011/071943 | 6/2011 |
| WO | WO 2011/127006 | 10/2011 |
| WO | WO 2011/127099 | 10/2011 |
| WO | WO 2011/155833 | 12/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/140224 | 10/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/071361 | 5/2014 |
| WO | WO 2014/130576 | 8/2014 |
| WO | WO 2014/144713 | 9/2014 |
| WO | WO 2014/152397 | 9/2014 |
| WO | WO 2014/163886 | 10/2014 |
| WO | WO 2014/210223 | 12/2014 |
| WO | WO 2014/210353 | 12/2014 |
| WO | WO 2015/031691 | 3/2015 |
| WO | WO 2015/069374 | 5/2015 |
| WO | WO 2015/085275 | 6/2015 |
| WO | WO 2015/161173 | 10/2015 |
| WO | WO 2016/077763 | 5/2016 |
| WO | WO 2016/126882 | 8/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/075293 | 5/2017 |
| WO | WO 2017/096158 | 7/2017 |
| WO | WO 2017/143155 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | 2018045186 | 3/2018 |
| WO | WO 2018/045181 | 3/2018 |
| WO | WO 2018/064640 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/175779 | 9/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047004 | 3/2020 |
| WO | WO 2020/047005 | 3/2020 |
| WO | WO 2020/047007 | 3/2020 |
| WO | WO 2020/047010 | 3/2020 |
| WO | WO 2020/056381 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |

(56) References Cited

FOREIGN PATENT DOCUMENTS

| WO | WO 2021/236929 | 11/2021 |
|---|---|---|
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/076345 | 5/2023 |
| WO | WO 2023/086880 | 5/2023 |
| WO | WO 2023/102118 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |

OTHER PUBLICATIONS

Chen et al. "Arrayed profiling of multiple glycans on whole living cell surfaces." Analytical chemistry, Oct. 15, 2013, 85(22):11153-11158.
Choi et al., "Multiplexed detection of mRNA using porosity-tuned hydrogel microparticles," Analytical chemistry, Sep. 28, 2012, 84(21):9370-9378.
Fan et al., "A versatile assay for high-throughput gene expression profiling on universal array matrices," Genome Research, May 1, 2004, 14(5):878-885.
Sun et al., "Statistical Analysis of Spatial Expression Pattern for Spatially Resolved Transcriptomic Studies," Nature Methods, Jan. 27, 2020, 17(2): 193-200.
Svensson et al., "SpatialDE: identification of spatially variable genes," Nature Methods, May 2018, 15:343-346, 15 pages.
U.S. Appl. No. 13/080,616, filed Oct. 6, 2011, Chee.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No. Author Listed], "Microarray technologies have excellent possibilities in genomics-related researches," Science Tools From Amersham Pharmacia Biotech, 1998, 3(4): 8 pages (with English Translation).
[No. Author Listed], "Proseek® Multiplex 96×96 User Manual," Olink Proteomics, Olink Bioscience, Uppsala, Sweden, 2017, 20 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 70 pages.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Agbavwe et al., "Efficiency, error and yield in light-directed maskless synthesis of DNA microarrays," Journal of Nanobiotechnology, Dec. 2011, 9:57, 17 pages.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal G·T Mismatches in DNA," Biochemistry, 1996, 36(34):10581-10594.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Andresen et al., "Deciphering the Antibodyome—Peptide Arrays for Serum Antibody Biomarker Diagnostics," Current Proteomics, 6(1):1-12, 2009.
Andresen et al., "Helicase-dependent amplification: use in OnChip amplification and potential for point-of-care diagnostics," Expert Rev Mol Diagn., Oct. 2009, 9(7):645-650.

(56) References Cited

OTHER PUBLICATIONS

Appella, "Non-natural nucleic acids for synthetic biology," Current Opinion in Chemical Biology, Dec. 2009, 13(5-6): 687-696.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al., "2D-PCR: a method of mapping DNA in tissue sections," Lab Chip, 2009, 9(24):3526-34.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Asp et al., "Spatially Resolved Transcriptomes-Next Generation Tools for Tissue Exploration," Bioessays, Oct. 2020, 42(10):e1900221, 16 pages.
Atkinson et al., "An Updated Protocol for High Throughput Plant Tissue Sectioning, " Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.
Baner et al., "Signal amplification of padlock probes by rolling circle replication," Nucleic Acids Res., 1998, 26(22):5073-5078.
Barnes, "PCR amplification of up to 35-kb DNA with high fidelity and high yield from lambda bacteriophage templates," Proc. Natl. Acad. Sci USA, 1994, 91(6):2216-2220.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Beier et al., "Versatile derivatisation of solid support media for covalent bonding on DNA-microchips," Nucleic Acids Res., May 1999, 27(9):1970-7.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Birney et al., "Identification and analysis of functional elements in 1% of the human genome by the ENCODE pilot project, " Nature, 2007, 447(7146):799-816.
Blair et al., "Microarray temperature optimization using hybridization kinetics," Methods Mol Biol., 2009, 529:171-96.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.

Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).
Boulé et al., "Terminal deoxynucleotidyl transferase indiscriminately incorporates ribonucleotides and deoxyribonucleotides," J Biol Chem., Aug. 2001, 276(33):31388-93.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein, " Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4, " Biochem. J. 2006, 398(1):135-144.
Bunt et al., "FRET from single to multiplexed signaling events," Biophys Rev. Apr. 2017, 9(2): 119-129.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections, " Biotechniques, 1998, 24(1):92-100.
Caliari et al., "A practical guide to hydrogels for cell culture," Nat Methods., Apr. 2016, 13(5):405-14.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chatterjee et al., "Protein Microarray On-Demand: A Novel Protein Microarray System," PLos One, 2008, 3(9):e3265, 5 pages.
Chen et al., "DNA hybridization detection in a microfluidic Channel using two fluorescently labelled nucleic acid probes, " Biosensors and Bioelectronics, 2008, 23(12):1878-1882.
Chen et al., "Efficient in situ barcode sequencing using padlock probe-based BaristaSeq," Nucleic Acids Res., 2018, 46(4): e22, 11 pages.
Chen et al., "Expansion microscopy," Science, 2015, 347(6221):543-548.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.

(56) References Cited

OTHER PUBLICATIONS

Chen et al., "μCB-seq: microfluidic cell barcoding and sequencing for high-resolution imaging and sequencing of single cells," Lab Chip, Nov. 2020, 20(21):3899-3913.
Cheng et al., "Sensitive Detection of Small Molecules by Competitive Immunomagnetic-Proximity Ligation Assay," Anal Chem, 2012, 84:2129-2132.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Chrisey et al., "Covalent attachment of synthetic DNA to self-assembled monolayer films," Nucleic Acids Res., Aug. 1996, 24(15):3031-9.
Ciaccio et al., "Systems analysis of EGF receptor signaling dynamics with microwestern arrays," Nat Methods, Feb. 2010, 7(2):148-55.
Codeluppi et al., "Spatial organization of the somatosensory cortex revealed by osmFISH," Nature Methods, Nov. 2018, 15:932-935.
Condina et al., "A sensitive magnetic bead method for the detection and identification of tyrosine phosphorylation in proteins by MALDI-TOF/TOF MS," Proteomics, 2009, 9:3047-3057.
Constantine et al., "Use of genechip high-density oligonucleotide arrays for gene expression monitoring," Life Science News, Amersham Life Science, 1998, pp. 11-14.
Corces et al., "An improved ATAC-seq protocol reduces background and enables interrogation of frozen tissues, " Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by Nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Dean et al., "Rapid Amplification Of Plasmid And Phage DNA Using Phi29 DNA Polymerase And Multiply-Primed Rolling Circle Amplification," Genome Research, Jun. 2001, 11:1095-1099.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "Accurate sequencing by hybridization for DNA diagnostics and individual genomics," Nature Biotechnology, 16:54-58, 1998.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA, " BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Escholarship.org [online], "Methods and devices for fabricating and assembling DNA and protein arrays for high-throughput analyses [electronic resource]," 2010, retrieved on Jun. 8, 2022, retrieved from URL<https://escholarship.org/uc/item/6tf7p46s>, 155 pages.
Evers et al., "The effect of formaldehyde fixation on RNA: optimization of formaldehyde adduct removal," J Mol Diagn., May 2011, 13(3):282-8.
Faruqi et al., "High-throughput genotyping of single nucleotide polymorphisms with rolling circle amplification," BMC Genomics, Aug. 2001, 2:4, 10 pages.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency, " bioRxiv, 2021, 20 pages.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gansauge et al., "Single-stranded DNA library preparation from highly degraded DNA using T4 DNA ligase," Nucleic Acids Res., Jun. 2017, 45(10):e79, 10 pages.
Gao et al., "A highly homogeneous expansion microscopy polymer composed of tetrahedron-like monomers," bioRxiv, Oct. 22, 2019, 23 pages (Preprint).
Gao et al., "Q&A: Expansion microscopy," BMC Biology, 15:50, 9 pages, 2017.

(56) References Cited

OTHER PUBLICATIONS

Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in Drosophila," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging In Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goransson et al., "A single molecule array for digital targeted molecular analyses," Nucleic Acids Res., Nov. 25, 2009, 37(1):e7, 9 pages.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hanauer et al., "Separation of nanoparticles by gel electrophoresis according to size and shape, " Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount *Arabidopsis* samples," Nature Protocols, 2006, 1(4):1939-1946.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains, " PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hoffman et al., "Formaldehyde crosslinking: a tool for the study of chromatin complexes," J Biol Chem., Oct. 2015, 290(44):26404-11.
Hölz et al., "High-Efficiency Reverse (5'->3') Synthesis of Complex DNA Microarrays," Scientific Reports, Oct. 2018, 8(1):15099, 12 pages.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1):121-4.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jennane et al., "Photolithography of self-assembled monolayers: optimization of protecting groups by an electroanalytical method, " Can. J Chem., Dec. 1996, 74(12):2509-2517.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Joos et al., "Covalent attachment of hybridizable oligonucleotides to glass supports," Anal Biochem., Apr. 1997, 247(1):96-101.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Kap et al., "Histological assessment of PAXgene tissue fixation and stabilization reagents," PLoS One, 2011, 6:e27704, 10 pages.

(56) References Cited

OTHER PUBLICATIONS

Kapteyn et al., "Incorporation of non-natural nucleotides into template-switching oligonucleotides reduces background and improves cDNA synthesis from very small RNA samples, " BMC Genomics, Jul. 2010, 11:413, 9 pages.

Karmakar et al., "Organocatalytic removal of formaldehyde adducts from RNA and DNA bases," Nature Chemistry, Aug. 3, 2015, 7(9):752-758.

Kaya-Okur et al., "CUT&Tag for efficient epigenomic profiling of small samples and single cells," Apr. 2019, 10(1):1930, 10 pages.

Ke et al., "In situ sequencing for RNA analysis in preserved tissue and cells," Nat Methods., Sep. 2013, Supplementary Materials, 29 pages.

Kennedy-Darling et al., "Measuring the Formaldehyde Protein-DNA Cross-Link Reversal Rate," Analytical Chemistry, 2014, 86(12):5678-5681.

Kent et al., "Polymerase θ is a robust terminal transferase that oscillates between three different mechanisms during end-joining" Elife, Jun. 2016, 5:e13740, 25 pages.

Kirby et al., "Cryptic plasmids of Mycobacterium avium: Tn552 to the rescue, " Mol Microbiol., Jan. 2002, 43(1):173-86.

Kleckner et al., "Tn10 and IS10 transposition and chromosome rearrangements: mechanism and regulation in vivo and in vitro," Curr Top Microbiol Immunol., 1996, 204:49-82.

Koch et al., "Photochemical immobilization of anthraquinone conjugated oligonucleotides and PCR amplicons on solid surfaces, " Bioconjugate Chem., Jul. 2000, 11(4):474-483.

Korbel et al., "Paired-end mapping reveals extensive structural variation in the human genome," Science, 2007, 318(5849):420-426.

Korlach et al., "Selective aluminum passivation for targeted immobilization of single DNA polymerase molecules in zero-mode waveguide nanostructures," Proc. Natl. Acad. Sci. USA, 2008, 105:1176-1181.

Kozlov et al., "A highly scalable peptide-based assay system for proteomics," PLoS ONE, 2012, 7(6):e37441, 10 pages.

Kozlov et al., "A method for rapid protease substrate evaluation and optimization," Comb Chem High Throughput Screen, 2006, 9(6):481-87.

Kretschy et al., "Next-Generation o-Nitrobenzyl Photolabile Groups for Light-Directed Chemistry and Microarray Synthesis," Angewandte Chemie International Edition, Jul. 2015, 54(29):8555-8559.

Kristensen et al., "High-Throughput Methods for Detection of Genetic Variation," BioTechniques, Feb. 2001, 30(2):318-332.

Krzywkowski et al., "Chimeric padlock and iLock probes for increased efficiency of targeted RNA detection," RNA, Jan. 2019, 25(1):82-89.

Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.

Kumar et al., "Template-directed oligonucleotide strand ligation, covalent intramolecular DNA circularization and catenation using click chemistry," J Am Chem Soc., May 2007, 129(21):6859-64.

Kurz et al., "cDNA—protein fusions: covalent protein—gene conjugates for the in vitro selection of peptides and proteins," ChemBioChem., 2001, 2(9):666-72.

Kwok, "High-throughput genotyping assay approaches," Pharmocogenomics, Feb. 2000, 1(1):95-100.

Lage et al., "Whole genome analysis of genetic alterations in small DNA samples using hyperbranched strand displacement amplification and array-CGH," Genome Research, 2003, 13(2):294-307.

Lahiani et al., "Enabling Histopathological Annotations on Immunofluorescent Images through Virtualization of Hematoxylin and Eosin," J Pathol Inform., Feb. 2018, 9:1, 8 pages.

Lampe et al., "A purified mariner transposase is sufficient to mediate transposition in vitro," Embo J., Oct. 1996, 15(19):5470-9.

Landegren et al., "Reading bits of genetic information: methods for single-nucleotide polymorphism analysis," Genome Res., Aug. 1998, 8(8):769-76.

Langdale et al., "A rapid method of gene detection using DNA bound to Sephacryl," Gene, 1985, 36(3):201-210.

Larman et al., "Autoantigen discovery with a synthetic human peptidome," Nature Biotechnology, May 2011, 29(6):535-541.

Larman et al., "Sensitive, multiplex and direct quantification of RNA sequences using a modified RASL assay," Nucleic Acids Research, 2014, 42(14):9146-9157.

Lee et al., "Fluorescent in situ sequencing (FISSEQ) of RNA for gene expression profiling in intact cells and tissues, " Nature Protocols, 2015, 10(3):442-458.

Lee et al., "Improving the efficiency of genomic loci capture using oligonucleotide arrays for high throughput resequencing, " BMC Genomics, Dec. 2009, 10:646, 12 pages.

Leriche et al., "Cleavable linkers in chemical biology," Bioorganic & Medicinal Chemistry, 2012, 20:571-582.

Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.

Li et al., "A photocleavable fluorescent nucleotide for DNA sequencing and analysis," Proc. Natl. Acad. Sci., 2003, 100(2):414-419.

Li et al., "An activity-dependent proximity ligation platform for spatially resolved quantification of active enzymes in single cells," Nat Commun, Nov. 2017, 8(1):1775, 12 pages.

Li et al., "RASL-seq for Massively Parallel and Quantitative Analysis of Gene Expression," Curr Protoc Mol Biol., Apr. 2012, 4(13):1-10.

Li et al., "Review: a comprehensive summary of a decade development of the recombinase polymerase amplification," Analyst, Dec. 2018, 144(1):31-67.

Lietard et al., "High-Density RNA Microarrays Synthesized In Situ by Photolithography," Angew. Chem. Int. Ed. Engl., Nov. 2018, 57(46):15257-15261.

Lin et al., "Highly multiplexed imaging of single cells using a high-throughput cyclic immunofluorescence method," Nat Commun., Sep. 2015, 6:8390, 7 pages.

Linnarsson, "Recent advances in DNA sequencing methods—general principles of sample preparation, " Experimental Cell Research, 2010, 316(8):1339-1343.

Liu et al., "An integrated and sensitive detection platform for biosensing application based on Fe@Au magnetic nanoparticles as bead array carries," Biosens Bioelectron, Dec. 2010, 26(4):1442-8.

Liu et al., "High-Spatial-Resolution Multi-Omics Atlas Sequencing of Mouse Embryos via Deterministic Barcoding in Tissue," BioRxiv, 2019, 55 pages.

Liu et al., "High-Spatial-Resolution Multi-Omics Sequencing via Deterministic Barcoding in Tissue," Cell, Nov. 13, 2020, 183(6):1665-1681, 36 pages.

Liu et al., "Spatial transcriptome sequencing of FFPE tissues at cellular level," bioRxiv 788992, Oct. 14, 2020, 39 pages.

Liu et al., "Surface and interface control on photochemically initiated immobilization," J Am Chem Soc., Nov. 2006, 128(43):14067-72.

Lizardi et al., "Mutation detection and single-molecule counting using isothermal rolling-circle amplification," Nat. Genet., 1998, 19(3):225-232.

Lou et al., "A review of room temperature storage of biospecimen tissue and nucleic acids for anatomic pathology laboratories and biorepositories," Clin Biochem., Mar. 2014, 47(4-5):267-73.

Lovatt et al., "Transcriptome in vivo analysis (TIVA) of spatially defined single cells in live tissue," Nature Methods, 2013, 11(2):190-196.

Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.

Lundberg et al., "High-fidelity amplification using a thermostable DNA polymerase isolated from Pyrococcus furiosus," Gene, 1991, 108(1):1-6.

Lundberg et al., "Homogeneous antibody-based proximity extension assays provide sensitive and specific detection of low-abundant proteins in human blood," Nucleic Acids Res., 2011, 39(15):e102, 8 pages.

(56) References Cited

OTHER PUBLICATIONS

Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality DNA, RNA and protein analysis," Nucleic Acids Res., Jun. 2007, 35(12):e85, 10 pages.
Ma et al., "Isothermal amplification method for next-generation sequencing," PNAS, Aug. 12, 2013, 110(35):14320-14323.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Marx, "Method of the Year: spatially resolved transcriptomics," Nature Methods, 2021, 18(1):9-14.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
McCloskey et al., "Encoding PCR products with batch-stamps and barcodes," Biochem. Genet., 2007, 45(11-12):761-767.
Meers et al., "Improved CUT&RUN chromatin profiling tools," Elife, Jun. 2019, 8:e46314, 16 pages.
Mcgee, "Structure and Analysis of Affymetrix Arrays," UTSW Microarray Analysis Course, Oct. 28, 2005, 68 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans- chromatin interaction networks using chromosome conformation capture (3C)," Methods Mol Biol., 2009, 464:105-21.
Mignardi et al., "Oligonucleotide gap-fill ligation for mutation detection and sequencing in situ," Nucleic Acids Research, Aug. 3, 2015, 43(22):e151, 12 pages.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Miner et al., "Molecular barcodes detect redundancy and contamination in hairpin-bisulfite PCR," Nucleic Acids Res., Sep. 2004, 32(17):e135, 4 pages.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mitsuhashi et al., "Gene manipulation on plastic plates," Nature 357: 519-520, 1992.
Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3A," Gene, 1982, 20(3):317-322.
Mohsen et al., "The Discovery of Rolling Circle Amplification and Rolling Circle Transcription," Acc Chem Res., Nov. 15, 2016, 49(11):2540-2550, 25 pages.
Morlan et al., "Selective depletion of rRNA enables whole transcriptome profiling of archival fixed tissue," PLoS One, Aug. 2012, 7(8):e42882, 8 pages.
Motea et al., "Terminal deoxynucleotidyl transferase: the story of a misguided DNA polymerase," Biochim Biophys Acta., May 2010, 1804(5):1151-66.
Mulder et al., "CapTCR-seq: hybrid capture for T-cell receptor repertoire profiling," Blood Advances, Dec. 2018, 2(23):3506-3514.
Nadji et al., "Immunohistochemistry of tissue prepared by a molecular-friendly fixation and processing system," Appl Immunohistochem Mol Morphol., Sep. 2005, 13(3):277-82.
Nallur et al., "Signal amplification by rolling circle amplification on DNA microarrays," Nucleic Acids Res., Dec. 1, 2001, 29(23):e118, 9 pages.
Nandakumar et al., "How an RNA Ligase Discriminates RNA versus DNA Damage," Molecular Cell, 2004, 16:211-221.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4.
Niedringhaus et al., "Landscape of next-generation sequencing technologies," Anal Chem., Jun. 2011, 83(12):4327-41.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "RNA-templated DNA ligation for transcript analysis," Nucleic Acids Res., Jan. 2001, 29(2):578-81.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Oleinikov et al., "Self-assembling protein arrays using electronic semiconductor microchips and in vitro translation," J Proteome Res, May-Jun. 2003, 2(3): 313-319.
Olivier, "The Invader assay for SNP genotyping," Mutat. Res., Jun. 2005, 573(1-2):103-110.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Ozsolak et al., "Digital transcriptome profiling from attomole-level RNA samples," Genome Res., Apr. 2010, 20(4):519-25.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Passow et al., "RNAlater and flash freezing storage methods nonrandomly influence observed gene expression in RNAseq experiments, " bioRxiv, Jul. 2018, 28 pages.
PCT International Preliminary Report on Patentability in International Appln. No. PCT/US2019/048425, dated Mar. 2, 2021, 9 pages.

(56) References Cited

OTHER PUBLICATIONS

PCT International Preliminary Report on Patentability in International Appln. No. PCT/US2019/048434, dated Mar. 2, 2021, 15 pages.
PCT International Search Report and Written Opinion in International Appln. No. PCT/US2020/066681, dated Apr. 14, 2021, 17 pages.
PCT International Search Report and Written Opinion in International Appln. No. PCT/US2021/012659, dated Apr. 16, 2021, 15 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gen," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Plasterk, "The Tcl/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Raj et al., "Imaging individual mRNA molecules using multiple singly labeled probes," Nature Methods, Oct. 2008, 5(10):877-879, 9 pages.
Ramachandran et al., "Next-generation high-density self-assembling functional protein arrays," Nature Methods, Jun. 2008, 5(6):535-538.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Rogers et al., "Immobilization of oligonucleotides onto a glass support via disulfide bonds: A method for preparation of DNA microarrays," Anal Biochem., Jan. 1999, 266(1):23-30.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res., Jan. 2001, 11(1):3-11.
Rouillard et al., "OligoArray 2.0: design of oligonucleotide probes for DNA microarrays using a thermodynamic approach," Nuc. Acid Research, Jun. 2003, 31(12): 3057-3062.
Roy et al., "Assessing long-distance RNA sequence connectivity via RNA-templated DNA-DNA ligation," eLife, 2015, 4:e03700, 21 pages.
Rubina et al., "Hydrogel-based protein microchips: manufacturing, properties, and applications," Biotechniques, May 2003, 34(5):1008-14.
Running et al., "A procedure for productive coupling of synthetic oligonucleotides to polystyrene microtiter wells for hybridization capture," Biotechniques, Mar. 1990, 8(3):276-279.
Sack et al., "Express photolithographic DNA microarray synthesis with optimized chemistry and high-efficiency photolabile groups," Journal of Nanobiotechnology, Mar. 2016, 14:14, 13 pages.
Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schlapak et al., "Glass surfaces grafted with high-density poly (ethylene glycol) as substrates for DNA oligonucleotide microarrays," Langinuir, Jan. 2006, 22: 277-285.
Schouten et al., "Relative quantification of 40 nucleic acid sequences by multiplex ligation-dependent probe amplification," Nucleic Acids Res., Jun. 2002, 30(12):e57, 13 pages.
Schwartz et al., "Capturing native long-range contiguity by in situ library construction and optical sequencing," PNAS, Nov. 13, 2012, 109(46):18749-18754.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Seurynck-Servoss et al., "Evaluation of Surface Chemistries for Antibody Microarrays," Anal Biochem., 371(1):105-115, 2007.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.

(56) References Cited

OTHER PUBLICATIONS

Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, Apr. 2010, 107(16):7407-12.
Sountoulidis et al., "SCRINSHOT, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Sutherland et al., "Utility of formaldehyde cross-linking and mass spectrometry in the study of protein-protein interactions," J. Mass Spectrom., Jun. 2008, 43(6):699-715.
Takei et al., "Integrated Spatial Genomics Reveals Global Architecture Of Single Nuclei," Nature, Jan. 27, 2021, 590(7845):344-350, 53 pages.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Timofeev et al., "Regioselective immobilization of short oligonucleotides to acrylic copolymer gels," Nucleic Acids Res., Aug. 1996, 24(16):3142-8.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue," PLoS ONE, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.

Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Van Ness et al., "A versatile solid support system for oligodeoxynucleotide probe-based hybridization assays", Nucleic Acids Res., 19:3345-3350, 1991.
Vandenbroucke et al., "Quantification of splice variants using real-time PCR, " Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Wang et al., "Tagmentation-based whole-genome bisulfite sequencing," Nature Protocols, Oct. 2013, 8(10):2022-2032.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing," Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.

(56) References Cited

OTHER PUBLICATIONS

Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Yeakley et al., "A trichostatin A expression signature identified by TempO-Seq targeted whole transcriptome profiling, " PLoS One, May 2017, 12(5):e0178302, 22 pages.
Yeakley et al., "Profiling alternative splicing on fiber-optic arrays," Nature biotechnology, 2002, 20:353-358.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zhang et al., "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Genome-wide open chromatin regions and their effects on the regulation of silk protein genes in Bombyx mori," Sci Rep., Oct. 2017, 7(1):12919, 9 pages.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zhao et al., "Isothermal Amplification of Nucleic Acids," Chemical Reviews, Nov. 2015, 115(22):12491-12545.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.

Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Zahra et al., "Assessment of Different Permeabilization Methods of Minimizing Damage to the Adherent Cells for Detection of Intracellular RNA by Flow Cytometry, " Avicenna Journal of Medical Biotechnology, Jan. 1, 2014, 6(1):38-46.
Stahl, Patrick, et al., "Visualization and analysis of gene expression in tissue sections by spatial transcriptomics", SCIENCE, 353: 78-82; Jul. 1, 2016.
Visium Spatial Gene Expression Reagent Kits—User Guide; Document No. CG000239; Revision, RevA; Revision Date, Nov. 2019.
Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.
Belton et al., "Hi-C: A comprehensive technique to capture the conformation of genomes," Methods, Nov. 2012, 58(3):268-276, 16 pages.
Bentzen et al., "Large-scale detection of antigen-specific T cells using peptide-MHC-I multimers labeled with DNA barcodes," Nat Biotechnol., Oct. 2016, 34(10):1037-1045, 12 pages.
Fan et al., "Illumina Universal Bead Arrays," Methods in Enzymology, 2006, 410:57-73.
Hadrup et al., "Parallel detection of antigen-specific T-cell responses by multidimensional encoding of MHC multimers," Nat. Methods., Jul. 2009, 6(7), 520-526.
Mamedov et al., "Preparing unbiased T-cell receptor and antibody cDNA libraries for the deep next generation sequencing profiling," Frontiers in Immunol., Dec. 23, 2013, 4(456):1-10.
Oksuz et al., "Systematic evaluation of chromosome conformation capture assays," Nature Methods, Sep. 2021, 18:1046-1055.
Rohland et al., "Partial uracil-DNA-glycosylase treatment for screening of ancient DNA," Phil. Trans. R. Soc. B, Jan. 19, 2015, 370(1660): 20130624, 11 pages.
Su et al., "Restriction enzyme selection dictates detection range sensitivity in chromatin conformation capture-based variant-to-gene mapping approaches," bioRxiv, Dec. 15, 2020, 22 pages.
Hobro et al., "An evaluation of fixation methods: Spatial and compositional cellular changes observed by Raman imaging," Vibrational Spectroscopy, Jul. 2017, 91:31-45.
Howell et al., "iFRET: An Improved Fluorescence System for DNA-Melting Analysis," Genome Research, 2002, 12:1401-1407.
Landegren et al., "A Ligase-Mediated Gene Detection Technique," Science, 1988, 241(4869):1077-1080.
Lin et al., "Replication of DNA microarrays from zip code masters," J. Am. Chem. Soc., 2006, 128(10):3268-3272.
Nam et al., "Nanoparticle-Based Bio-Bar Codes for the Ultrasensitive Detection of Proteins," Science, Sep. 26, 2003, 301(5641):1884-1886.
Redmond et al., "Single-cell TCRseq: paired recovery of entire T-cell alpha and beta chain transcripts in T-cell receptors from single-cell RNAseq," Genome Med, 2016, 8:80, 12 pages.
Schmidl et al., "ChIPmentation: fast, robust, low-input ChIP-seq for histones and transcription factors," Nature Methods, Oct. 2015, 12:963-965.

\* cited by examiner

CAPTURING OLIGONUCLEOTIDES IN SPATIAL TRANSCRIPTOMICS

FIELD

This invention relates to improved capturing of biological analytes using spatial transcriptomics systems, especially when biological analytes are located remote from the surface of a biological tissue sample. The invention specifically relates to extended and/or branched capture probes that reach into a tissue sample and/or increase capture probe density within the tissue sample. The system and methods disclosed increase the analyte capturing potential of spatial transcriptomics arrays.

BACKGROUND

The field of spatial transcriptomics encompasses systems and methods for obtaining spatially informative data on expression of analytes, typically mRNAs, from hundreds to thousands of individual cells in a tissue.

In some examples of these systems and methods, a tissue section is overlaid onto a planar, high-density array of oligonucleotides that are attached to a support. The oligonucleotides of the array encode spatial barcodes, which identify the spatial location of individual oligonucleotides on the support. The oligonucleotides also encode analyte-capture domains that can capture specific analytes released from the overlying cells (e.g., by hybridization of the oligonucleotide's analyte-capture domain to specific analyte mRNAs from the cells). The analyte capture domains are linked to a unique molecular identifier or UMI encoded in the oligonucleotides. The UMI uniquely identifies the captured analyte.

When cells of a tissue overlaid onto an oligonucleotide array are permeabilized, analytes are released from the cells and diffuse to the surface of the array, where the analytes contact the oligonucleotides of the array. When a migrating analyte contacts an analyte-capture domain that is specific for that analyte, the analyte is captured by that oligonucleotide. Nucleotide sequencing of oligonucleotides that have captured analytes identifies the analyte, the UMI, as well as the spatial barcode of the oligonucleotide. This information provides for assignment of specific captured analytes to specific spatial locations on the array where the analytes were captured.

Additionally, imaging of the original tissue section, and the array including fiducial markers onto which the tissue section was overlaid, provides for assignment of specific cells of the tissue to specific spatial locations on the array that directly underlie the cells. Image and sequencing correlation of the locations of individual cells on the array, with the analytes captured at those locations, yields a spatial map of analyte expression for the cells of the tissue.

Systems, reagents and methods for improving spatial transcriptomic interrogation of tissues are actively being developed.

SUMMARY

Disclosed here are extended and/or branched assemblies of analyte capture probes for use in spatial transcriptomics systems. These capture probe assemblies extend, from the surface of an oligonucleotide array, into an overlaid tissue section. The branching nature of the capture probe assemblies increases the density of capture domains within a space in the tissue section. Because of their extended and branching properties, the capture probe assemblies capture more analytes (i.e., decrease the probability that an analyte will not be captured) and decrease the distance an analyte may have to migrate after release from a cell before it contacts a capture probe, as compared to conventional capture probe arrangements. The extended/branched capture probe assemblies, therefore, increase resolution of spatial transcriptomics systems. Disclosed are methods for making an assembly of oligonucleotide probes comprising: i) providing an oligonucleotide array that includes a support having a plurality of first probes affixed to the support, the plurality of first probes including a first nucleotide hybridization sequence; and ii) contacting the oligonucleotide array with: a) a plurality of second probes that include a second nucleotide hybridization sequence and a third nucleotide hybridization sequence, wherein the second nucleotide hybridization sequence is complementary to the first nucleotide hybridization sequence; and b) with a plurality of third probes that include a fourth nucleotide hybridization sequence complementary to the third nucleotide hybridization sequence; wherein the contacting is performed under conditions such that the first nucleotide hybridization sequence of the first probes is hybridized to the second nucleotide hybridization sequence of the second probes, and such that the third nucleotide hybridization sequence of the second probes is hybridized to the fourth nucleotide hybridization sequence of the third probes. Additionally, the contacting of the plurality of first probes, second probes and third probes may be done simultaneously; and wherein the method additionally includes: iii) first, hybridizing the plurality of first probes to the plurality of second probes at or below the first melting temperature; and iv) second, hybridizing the plurality of second probes to the plurality of third probes at or below the second melting temperature, but at a temperature greater than the first melting temperature.

Also disclosed are compositions comprising: i) an oligonucleotide array, including a support having a plurality of first probes affixed to the support, the plurality of first probes including a first nucleotide hybridization sequence; and ii) a plurality of second probes including a second hybridization sequence complementary to the first nucleotide hybridization sequence; wherein the first nucleotide hybridization sequence of the first probes is hybridized to the second nucleotide hybridization sequence of the second probes. Additionally, the plurality of second probes may include a third nucleotide hybridization sequence, and additionally comprising: iii) a plurality of third probes including a fourth nucleotide hybridization sequence complementary to the third nucleotide hybridization sequence; wherein the third nucleotide hybridization sequence of the second probes is hybridized to the fourth nucleotide hybridization sequence of the third probes In some examples, a melting temperature for a duplex formed by hybridization of the first nucleotide hybridization sequence with the second nucleotide hybridization sequence is greater than a melting temperature for a duplex formed by hybridization of the third nucleotide hybridization sequence with the fourth nucleotide hybridization sequence.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

The following U.S. patents and U.S. published patent applications are each incorporated by reference in their entirety into this application:

U.S. Pat. No. 9,593,365 (Ser. No. 14/434,274), issued Mar. 14, 2017 and titled, "Methods and Product for Optimising Localized or Spatial Detection of Gene expression in a Tissue Sample";

U.S. Pat. No. 10,030,261 (Ser. No. 14/111,482), issued Jul. 24, 2018 and titled, "Method and Product for Localized or Spatial Detection of Nucleic Acid in a Tissue Sample";

U.S. Pat. No. 10,774,374 (Ser. No. 15/565,637), published Jul. 4, 2019 and titled, "Spatially Distinguished, Multiplex Nucleic Acid Analysis of Biological Specimens;

U.S. Pat. No. 10,550,429 (Ser. No. 16/426,762), issued Feb. 4, 2020 and titled, "Methods and Systems for Processing Polynucleotides"; and U.S. Pat. No. 10,590,244 (Ser. No. 16/178,430), issued Mar. 17, 2020 and titled, "Compositions, Methods, and Systems for Bead Formation Using Improved Polymers."

Other references incorporated by reference may be listed throughout the application.

BRIEF DESCRIPTION OF THE DRAWINGS

In the accompanying drawings, which are incorporated in and constitute a part of the specification, embodiments of the disclosed inventions are illustrated. It will be appreciated that the embodiments illustrated in the drawings are shown for purposes of illustration and not for limitation. It will be appreciated that changes, modifications and deviations from the embodiments illustrated in the drawings may be made without departing from the spirit and scope of the invention, as disclosed below.

DETAILED DESCRIPTION

Figure 1:
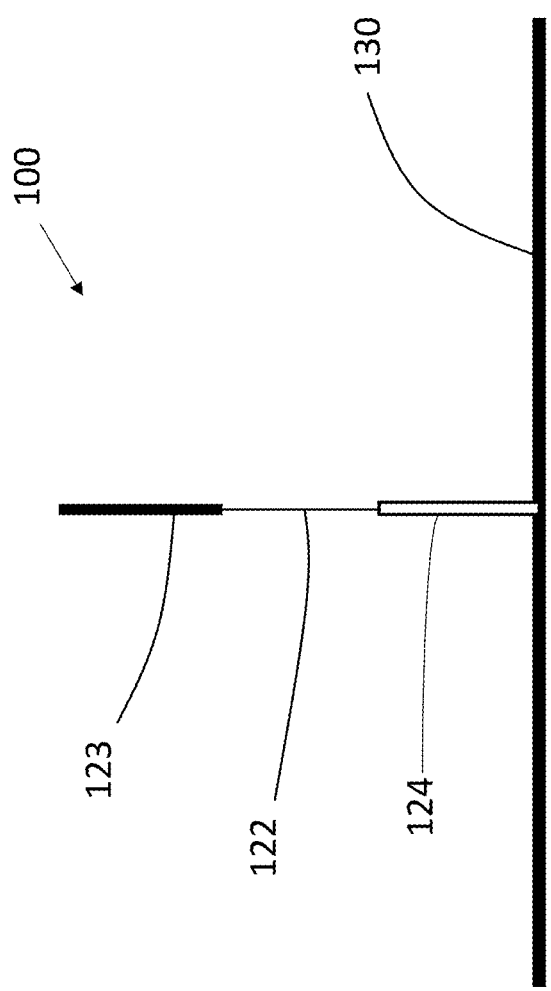
FIG. 1 is a schematic drawing (side view) illustrating an example of a spatial array oligonucleotide capture probe.

Spatial arrays include oligonucleotide capture probes attached to a support. When a tissue section is overlaid onto the surface of an array and analytes are released from cells of the tissue, analytes from the cells migrate away from the cells, contact the capture probes of the spatial arrays and are bound by domains in the capture probes, called capture domains, that are specific for given analytes. However, capture probes may favor capture of analytes proximal to the surface of the tissue section in contact with the spatial array and may less efficiently capture analytes from cells located deeper within the tissue section. In some examples, capture probes may not extend far enough into the depth of the overlying three-dimensional tissue structure (e.g., 7-15 μm thickness) to contact analytes from cells located there. Even for analytes from cells that are proximal to the surface of the spatial array, the density of capture probes may not be high enough to prevent existence of "dead areas" in which there are no capture probes, or where there are not enough capture probes, to capture the available analytes. Consequently, analytes may not be captured or, when analytes are captured, they may be captured by capture probes that are distant from the cells that released the analytes. Capture of an analyte by a non-adjacent capture probe may limit the ability to map the analyte back to the location of the cell in the tissue section that actually released it and may degrade resolution of the spatial system.

The present disclosure provides systems and techniques for self-assembling multiple oligonucleotide probes into extended and/or branched scaffolds. The scaffolds extend the reach of capture probes to points distal from the surface of the spatial arrays and into the depth of the tissue section overlying a spatial array. Branching of the scaffolds increases the density of capture probes, prevents dead areas that contain no capture probes and lessens the probability that an analyte will not be captured. The branched scaffolds also increase resolution of the spatial array systems by decreasing the distance that an analyte has to migrate when released from a cell, before the analyte contacts and is captured by an oligonucleotide capture probe.

Definitions

Unless defined otherwise, all technical and scientific terms used herein have the same meaning as commonly understood by one of ordinary skill in the art to which the present invention pertains. It is to be understood that the terminology used herein is for describing particular embodiments only and is not intended to be limiting. For purposes of interpreting this disclosure, the following description of terms will apply and, where appropriate, a term used in the singular form will also include the plural form and vice versa.

Herein, "amplification product" refers to molecules that result from reproduction or copying of another molecule. Generally, the molecules copied or reproduced are nucleic acid molecules, specifically DNA or RNA molecules. In some examples, the molecule reproduced or copied may be used as a template for the produced molecules. In some examples, an analyte captured by the capture domain of an oligonucleotide may be used as a template to produce an amplification product. In some examples, an mRNA captured by the capture domain of an oligonucleotide may be used as a template to produce a cDNA amplification product. Various enzymes (e.g., reverse transcriptase) may be used for this process. The cDNA amplification product may in turn act as a template for amplification that may also be called amplification products. Various enzymes (e.g., Taq polymerase) may be used for this process.

Herein, "analyte" refers to a substance whose chemical constituents are being identified and/or measured. Generally, this application refers to analytes from and/or produced by cells. Any or all molecules or substance from or produced by a cell may be referred to herein as analytes. Chemically, cellular analytes may include proteins, polypeptides, peptides, saccharides, polysaccharides, lipids, nucleic acids, and other biomolecules.

Herein, "array" refers to a region on a support that contains multiple demarcated regions of oligonucleotides, interspersed with intervening regions that do not contain oligonucleotides. In some examples, these regions may be referred to as "oligonucleotide arrays" or "capture areas". The arrays herein generally have oligonucleotides that contain spatial barcodes and, thus, the arrays may be referred to as "spatial" arrays.

Herein, "associated with" generally describes a connection or relationship between two things. Herein, "associated with" may be used to refer to the results of one or more of at least three processes. The first process is cell segmentation, where individual cells overlaid onto an array are matched with or assigned to one or more array spots that are directly underneath the overlaid cells. The second process is assignment of analytes (e.g., nucleotide sequences), generally representing specific mRNAs from cells overlaid onto an array, to array spots that capture the specific mRNA, using spot-specific barcodes encoded by the oligonucleotides of the array. The third process is assignment of nucleotide sequences, representing specific mRNAs from cells overlaid onto an array, to specific cells overlaid onto the array.

Herein, "assembly," when used as a noun, refers to the layered configurations of oligonucleotide capture probes described herein. An assembled arrangement of capture probes may also be referred to as a scaffold. When used as a verb, "assembly" may refer to the process of building such a configuration of oligonucleotide capture probes.

Herein, "barcode," generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). Barcodes can have a variety of different formats. For example, barcodes can include polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads. In some examples, a barcode may be a nucleotide sequence that is encoded by, linked to or associated with one or more oligonucleotides. In some examples, a specific barcode may correlate with a location of a barcode, on a support, for example. A barcode used to convey locational information may be called a spatial barcode.

Herein, "barcoded molecule" or, in some examples, "barcoded nucleic acid molecule" generally refers to a molecule or a nucleic acid molecule that results from, for example, the processing of a nucleic acid barcode molecule with a nucleic acid sequence (e.g., nucleic acid sequence complementary to a nucleic acid primer sequence encompassed by the nucleic acid barcode molecule). The nucleic acid sequence may be a targeted sequence (e.g., targeted by a primer sequence) or a non-targeted sequence. For example, in the methods, systems and kits described herein, hybridization and reverse transcription of the nucleic acid molecule (e.g., a messenger RNA (mRNA) molecule) of a cell with a nucleic acid barcode molecule (e.g., a nucleic acid barcode molecule containing a barcode sequence and a nucleic acid primer sequence complementary to a nucleic acid sequence of the mRNA molecule) results in a barcoded nucleic acid molecule that has a sequence corresponding to the nucleic acid sequence of the mRNA and the barcode sequence (or a reverse complement thereof). A barcoded nucleic acid molecule may be a nucleic acid product. A barcoded nucleic acid molecule may serve as a template, such as a template polynucleotide, that can be further processed (e.g., amplified) and sequenced to obtain the target nucleic acid sequence. For example, in the methods and systems described herein, a barcoded nucleic acid molecule may be further processed (e.g., amplified) and sequenced to obtain the nucleic acid sequence of the mRNA as well as the sequence of the spatial barcode thereby determining the locational position of the mRNA along with its identity. Herein, molecules stated to have a "common barcode sequence" refers to molecules that are labeled or identified with the same barcode sequence.

Herein, "base-paired" generally refers to the situation where two complementary nucleic acids have formed hydrogen bonds between complementary nucleotides in the different strands. Two such nucleic acid strands may be referred to as hybridized to one another.

Herein, "branched" generally refers to a particular arrangement of oligonucleotide capture probes within an assembly that increases the density of capture domains in a space. Herein, "capable" means having the ability or quality to do something.

Herein, "capture" generally refers to the capability of a first substance to interact with and/or bind a second substance where, for example, the second substance is part of a population of other substances. An analyte may be captured. In some examples, capture refers to identification of a target nucleic acid molecule (e.g., an RNA) by its hybridization to a capture probe, and/or amplification of a target nucleic acid molecule or a nucleic acid probe hybridized to it (e.g., an RNA or a probe hybridized to the RNA) using, for example polymerase chain reaction (PCR) and/or nucleic acid extension of a target nucleic acid molecule or a capture probe hybridized to it using, for example reverse transcription reactions.

Herein, "capture probe" refers to a molecule (e.g., an oligonucleotide) that contains a capture domain.

Herein, "capture domain" means a part of a molecule that is capable of binding or capturing a substance. An analyte capture domain may be capable of capturing analytes that may include proteins, polypeptides, peptides, saccharides, polysaccharides, lipids, nucleic acids, and other biomolecules. In some examples, the analyte capture domain may be a nucleotide sequence capable of hybridizing to an analyte that contains a complementary nucleotide sequence. Herein, "nucleotide capture sequence" refers to a first nucleotide sequence that is capable of capturing (e.g., by hybridizing to) a second nucleotide sequence. In some examples, an analyte capture domain may contain modified nucleotides.

Herein, "cell block" refers to cells embedded in a medium. In some examples, the medium may be a gel, like agarose, hydrogel, polyacrylamide, OCT, and the like.

Herein, "complementary," in the context of one sequence of nucleic acids being complementary to another sequence, refers to the ability of two strands of single-stranded nucleic acids to form hydrogen bonds between the two strands, along their length. A complementary strand of nucleic acids is generally made using another nucleic acid strand as a template. A first nucleotide that is capable of hybridizing to a second nucleotide sequence may be said to be a complement of the second nucleotide sequence.

Herein, "configured to" generally refers to a component of a system that can perform a certain function.

Herein, "contact" refers to physical touching of separate substances or objects. "Contacting" refers to causing separate substances to physically touch one another.

Herein, "cryosection" refers to a section of a tissue or a cell block for visual or microscopic examination made from a fresh frozen sample by a cryostat. A cryosection is a type of "section" as defined herein.

Herein, "diffusion" refers to travel of an analyte released from a cell that is overlaid onto a spatial array, to capture probes that are not the capture probes nearest to the overlaid cell. See definition of "migration" for more detail.

Herein, "discrete" means separate or individual.

Herein, "duplex" refers to a double-strand nucleic acid. Herein, duplexes are generally formed between complementary hybridizing nucleotide sequences.

Herein, "extended" generally refers to a particular arrangement of oligonucleotide capture probes within an assembly that increase the length or reach of capture domains in a space.

Herein, "fix," refers to formation of covalent bonds, such as crosslinks, between biomolecules or within molecules. The process of fixing cells for example, is called "fixation." The agent that causes fixation is generally referred to as a "fixative" or "fixing agent." "Fixed cells" or "fixed tissues" refers to cells or tissues that have been in contact with a fixative under conditions sufficient to allow or result in formation of intra- and inter-molecular crosslinks between biomolecules in the biological sample. Fixation may be reversed and the process of reversing fixation may be referred to as "un-fixing" or "decrosslinking." Unfixing or decrosslinking refers to breaking or reversing the formation of covalent bonds in biomolecules formed by fixatives. Non limiting examples of fixatives or fixing agents include methanol, paraformaldehyde, formalin, and acetone to name a few.

Herein, "generate" means to make or produce. Generally, herein, generate is used to describe producing complementary nucleic acid molecules (e.g., making an amplification product) using a template nucleic acid molecule.

Herein, "hybridize" refers to a nucleotide sequence of a single-stranded nucleic acid molecule forming a complex with a nucleic acid molecule having a complementary nucleotide sequence. Generally, the complex forms through hydrogen bonding between complementary nucleotide bases in separate nucleic acid molecules.

Herein, "hybridizing nucleotide sequence" refers to a nucleotide sequence, within an oligonucleotide for example, that is capable of hybridizing with a complementary nucleotide sequence in a target nucleic acid molecule present on or within a cell from a tissue sample (e.g., cellular RNA). When a hybridizing nucleotide sequence is of such a length that it hybridizes with a complementary, either fully or partially, nucleotide sequence that is unique to a target nucleic acid molecule(s) (e.g., cellular RNA or family of RNAs), the hybridizing nucleotide sequence may be said to hybridize to the same target nucleic acid molecule (e.g., the same RNA).

Herein, "immobilize" means to restrict or prevent movement.

Herein, "in common" means a property, characteristic, feature, etc., that is possessed by separate things. Herein, "in common" may be used, for example, to refer to a nucleotide sequence that is possessed or encoded by two or more separate molecules.

Herein, "intermediate agent" refers to an identifier of a particular mRNA that is not itself the mRNA. In some examples, an intermediate agent of a particular mRNA may be a DNA sequence complementary to the mRNA (i.e., cDNA) or a DNA sequence complementary to the cDNA.

Herein, "intervening region" or "interspot space" refers to areas on a support of an array that do not contain attached oligonucleotides. Herein, "library" refers to a collection of molecules having nucleotide sequences that are generally representative (e.g., comprising the same nucleotide sequences or complementary nucleotide sequences) of nucleotide sequences present in the molecules from the target nucleic acids. Generally, the molecules from which a library is made act as templates for synthesis of the collection of molecules that make up the library. The "library" may be, or may be produced from, amplification products of the target nucleic acid. Herein, libraries can be created from amplification of a mRNA analyte, or copies thereof, captured on an array. Therefore, the library can be derived from the captured target nucleic acid.

Herein, "melting temperature" or "$T_m$" of a nucleic acid hybrid (i.e., two nucleic acid stands hybridized through hydrogen bonding) refers to a temperature at which hybridized nucleic acid strands become single-stranded. As known in the art, Tm may depend on the length of hybridizing nucleic acid sequences (i.e., the number nucleotides in the duplex), the base-pair composition of the duplex, as well as other factors. Generally, it is possible to design a duplex (e.g., see definition for "hybridizing nucleotide sequence") having a specific $T_m$, and/or to design a series of duplexes having a progression of $T_m$'s (e.g., three duplexes where the first has a relatively low $T_m$, the second has an intermediate $T_m$, and the third has a relatively high $T_m$).

Herein, "migration" refers to movement of an analyte from a cell that is overlaid onto a spatial array, to a capture probe that is attached to the surface of the array. In some examples of migration, analytes released from cells on an array may migrate in such a way that they contact capture probes located directly under the cell and/or are in contact with the cell. In other examples of migration, analytes released from cells on the array may migrate in such a way that they do not contact capture probes nearest the cell that released the analyte. Instead, at least some of the analytes released from a cell may travel away from the cells (e.g., laterally, orthogonally, etc.) and contact capture probes that are not nearest the cell that released the analyte. In some examples, the analytes may contact capture probes adjacent, or even not adjacent, to capture probes that lie underneath or contact the cells overlaid onto an array. Herein, travel of analytes to capture probes that are not those nearest to an overlaid cell is referred to as "diffusion." Diffusion is a type of migration. In the present disclosure, migration and diffusion are passive, unless otherwise stated.

Herein, "oligonucleotide" means a linear polymer of nucleotides, in some examples 2'-deoxyribonucleotides. Oligonucleotides are single stranded. Oligonucleotides can be of various lengths. Oligonucleotides can include modified nucleotides as known in the art.

Herein, "origin" refers to the source of something. Something that is stated to have a specific origin may be said to "originate" from that source.

Herein, "permeable" refers to something that allows certain materials to pass through it. "Permeable" may be used to describe a cell in which analytes in the cell can leave the cell. "Permeabilize" is an action taken to cause, for example, a cell to release its analytes. In some examples, permeabilization of a cell is accomplished by affecting the integrity of a cell membrane such as by application of a protease or other enzyme capable of disturbing a cell membrane allowing analytes to diffuse out of the cell.

Herein, "primer" means a single-stranded nucleic acid sequence that provides a starting point for DNA synthesis. Generally, a primer has a nucleotide sequence that is complementary to a template, and has an available 3'-hydroxyl group to which a transcriptase or polymerase can add additional nucleotides complementary to corresponding nucleotides in the template, to synthesize a nucleic acid strand in the 3' to 5' direction.

Herein, "print" means to apply something to a substrate or surface in a particular way or to a particular location. Printing refers to the act of applying something to a substrate.

Herein, "resolution" is generally used to describe the ability of a spatial analysis system to attribute, correlate or match expression of an analyte to one or more cells. High resolution is desirable and refers to the situation where expression of analytes can be ascribed to single cells.

Herein, "RNA capturing probe" refers to a nucleic acid molecule capable of hybridizing to an RNA.

Herein, "sample" or "biological sample" generally refers to a collection of cells or to a tissue. Generally, a tissue contains multiple cells, often similar cells that may perform the same or similar functions. The sample may be a cell sample. The sample may be a cell line or cell culture sample. The sample can include one or more cells, or one or more cell aggregates or clusters. The biological sample may be derived from another sample. The sample may be a tissue sample, such as a biopsy, core biopsy, needle aspirate, or fine needle aspirate. Example tissue types in animals may include connective, epithelial, brain, adipose, muscle and nervous tissue. The sample may be a fluid sample, such as a blood sample, urine sample, or saliva sample. The sample may be a skin sample. The sample may be a cheek swab. The sample may be a plasma or serum sample. In some examples, a sample may comprise any number of macromolecules, for example, cellular macromolecules or cellular analytes. The present disclosure is not limited to any particular type of tissue.

Herein, "section" generally refers to a thin layer or slice from a larger object.

Herein, "spatial" refers to a location within or on a space. In some examples, the space may be a two-dimensional space.

Herein, "species" generally refers to multiple oligonucleotides that have something in common. Generally, oligonucleotides considered to be part of the same species have at least one barcode in common. In some examples, the common barcode may be associated with a particular or a group of capture domain(s). In some examples, the common barcode may be associated with oligonucleotides on a support, for example, that are in proximity to one another. In some examples, the common barcode may be encoded by the oligonucleotides that are part of an array spot.

Herein, "spot" or "array spot" refers to an area on a support that contains a generally uninterrupted area of oligonucleotides attached to the support. Spots can also be referred to as "features". Generally, these areas have boundaries, beyond which, there may not be oligonucleotides attached to the support. An example array spot is shown as 208 in FIG. 2. In FIG. 3, multiple array spots 308 are shown on a support 330.

Herein, "support," when used as a noun, refers to something that serves, for example, as a foundation for another thing. In some examples, the support may be larger, more easily worked with, or more easily tracked or visualized than the thing being supported. A support may be a solid support. In some instances, a support may be dissolvable, disruptable, and/or degradable. In some cases, a support may not be degradable. A support may comprise glass, plastic, metal, and/or other substances. In some cases, the support can be rigid. In other cases, the support may be flexible and/or compressible. In some examples, a support may be referred to as a "substrate."

Herein, "surface" means the outside part or upper layer of something. Herein, a "surface" of an array generally refers to a surface of a support or substrate that has oligonucleotides attached.

Herein, "template" refers to one single-stranded nucleic acid acting as a "template" for synthesis of another complementary single-stranded nucleic acid. For example, RNA can act as a template for synthesis of a complementary DNA strand synthesized using reverse transcriptase. A single-stranded DNA can act as a template for synthesis of a complementary DNA strand, most often by a DNA polymerase.

Herein, "unique" means one of a kind or unlike something else. In some examples, a "unique" mRNA may refer to an mRNA encoded by a single-copy gene.

Herein, "unique molecular identifier" or "UMI" generally refers to an identifier of a particular analyte captured by a capture probe.

Obtaining Spatially Aligned Analyte Expression Data from Cells and Tissues

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample, including a mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample, it serves as a proxy for the analyte.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodriques et al., Science 363(6434): 1463-1467, 2019; Lee et al., Nat. Protoc. 10(3): 442-458, 2015; Trejo et al., PLOS ONE 14(2):e0212031, 2019; Chen et al., Science 348(6233):

aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. The above references, if US Patents or US Patent Publications, are incorporated herein by reference in their entirety. Further non-limiting aspects of spatial analysis methodologies and compositions are described herein.

Array-based spatial analysis methods involve the transfer of one or more analytes from a biological sample to an array of features (e.g., spots) on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent, including a ligation product or an analyte capture agent, or a portion thereof), or derivatives thereof (see, e.g., Section (II)(b)(vii) of WO 2020/176788 and/or U.S. Patent Application Publication No. 2020/0277663 regarding extended capture probes; incorporated herein by reference in their entirety). In some cases, capture probes may be configured to form ligation products with a template (e.g., a DNA or RNA template, such as an analyte or an intermediate agent, or portion thereof), thereby creating ligations products that serve as proxies for a template.

As used herein, an "extended capture probe" (as opposed to an extended assembly of capture probes, as described herein) refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; determination of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

In some cases, spatial analysis can be performed by detecting multiple oligonucleotides that hybridize to an analyte. In some instances, for example, spatial analysis can be performed using RNA-templated ligation (RTL). Methods of RTL have been described previously (See, e.g., Credle et al., Nucleic Acids Res. 2017 Aug. 21;45(14): e128). Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a two dimensional or three-dimensional map of the analyte presence and/or level.

In some cases, a map of analyte presence and/or level can be aligned to an image of a biological sample using one or more fiducial markers (e.g., objects placed in the field of view of an imaging system which appear in the image produced, as described in the Substrate Attributes Section and Control Slide for Imaging Section of WO 2020/123320). Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

Systems and methodologies in the field of spatial transcriptomics are designed to obtain spatially resolved analyte expression data (e.g., genomics, proteomics, transcriptomics) from tissues. In some examples, a tissue may be overlaid onto a support comprising barcoded oligonucleotides or capture probes. Generally, the oligonucleotides comprise a spatial barcode, which is correlated with and is an identifier for the location of the particular oligonucleotide on the support (e.g., in some examples, oligonucleotides having known barcode sequences are printed onto designated areas of the support). When analytes are released from a biological sample and migrate toward and contact the barcoded oligonucleotides, the barcoded oligonucleotides capture, or hybridize to, the analytes. In some examples, mRNAs may be the analytes and barcoded oligonucleotides may capture mRNAs having specific nucleotide sequences by hybridization, for example the barcoded oligonucleotides comprise a poly(T) capture domain that can hybridize a poly(A) tail of a mRNA. In the examples where mRNA is the analyte, reverse transcription of the captured mRNA can be initiated using added primers, and cDNA is produced using the barcoded oligonucleotide as a template. The resultant cDNA that is synthesized incorporates the barcodes included in the barcoded oligonucleotide or capture probe. The cDNAs may be amplified. A library of the cDNAs/amplified cDNAs is prepared and nucleotide sequences of the libraries are obtained. Nucleotide sequences of the spatial barcodes provides for the data for an mRNA transcript to be mapped back to its location on the support, and by also obtaining an image of the tissue and cells overlaid onto the support at the beginning of the procedure, mRNA transcripts may be mapped to the location in the overlaid tissue, where the mRNA was expressed.

In some examples, a planar support on the surface of which is attached a spatially ordered arrangement of barcoded oligonucleotides comprising analyte capture domains is used. In some examples, an analyte capture domain may be an oligo(dT) sequence for capturing poly(A) sequences of eukaryotic mRNA. Other sequences may be used to capture specific nucleic acids, including specific mRNAs. The arrangement of the oligonucleotides on the surface of the support can be known because the oligonucleotides comprise spatial barcodes. In some examples, the oligonucleotides, with known spatial barcodes, are printed in a known pattern onto specific, known areas of the surface of the planar support in a predetermined arrangement. A tissue is then applied to the surface of the support and analytes (e.g., mRNA) are released from the cells that make up the tissue. mRNAs released from the tissue migrate to the surface of the support and hybridize to oligo(dT) capture domain sequences of the attached oligonucleotides. The hybridized mRNAs are amplified using reverse transcription into complementary oligonucleotides that include sequences from the captured mRNA linked to the spatial barcode of the oligonucleotide to which the mRNA bound. Obtaining and decoding the nucleotide sequences of the complementary oligonucleotides reveals where on the support specific mRNAs bound to oligonucleotides. These locations are then correlated to regions of the tissue that was applied to the surface of the support.

In modifications of the above method, a tissue sample may be probed for expression of specific proteins using antibodies. The antibodies may have attached nucleotide tags having a specific nucleotide sequence that capture domains of the barcoded molecules on a support are designed to capture through hybridization. Thus, proteomic data can be obtained from the oligonucleotide arrays.

In modifications of the above method, a tissue sample may be probed for presence or absence of genetic mutations, variants, diversity, polymorphisms and the like in genomes, including single-nucleotide polymorphisms (SNPs) or single-nucleotide variants (SNVs) in genomes of cells making up the tissue. In some examples, a probe for a SNP or SNV may include a specific nucleotide sequence that can differentially hybridize to a genomic sequence dependent on whether a SNP or SNV is present. In some examples, a probe for a SNP or SNV may include a nucleotide sequence that can hybridize to a genomic sequence that is linked to (e.g., upstream of downstream of) a genomic region that might contain the SNP or SNV. Extension of the hybridized sequence, using the region of the genome that might contain the SNP/SNV as a template, and nucleotide sequencing of the extension product, may be used to determine if the SNP/SNV is present in the extension product. In some examples, probes for specific SNPS or SNVs may be part of the capture domain of certain oligonucleotides that make up the oligonucleotide array. Other techniques may be used to detect SNPs and/or SNVs.

In modifications of the above method, a tissue sample may be probed for isoforms of genes, transcripts (e.g., alternative transcription start sites, alternatively spliced mRNAs) or proteins. In some examples, a probe for an isoform of a gene or transcript may be designed to hybridize to one form but not the other, or may be designed to hybridize to or near a region that may contain the isoform such that amplification and/or extension of the hybridized probe, and optional nucleotide sequencing of the amplified product, can detect presence or absence of specific isoforms. In some examples, a probe for an isoform of a protein may be an antibody designed to differentially bind to the different isoforms. The antibodies used may have attached nucleotide tags that can capture domains of the barcoded molecules on a support, as described above.

Related to the invention disclosed herein, FIG. 1 is a schematic drawing (side view) that illustrates an example of a barcoded oligonucleotide 100. The oligonucleotide 100 is shown attached to a support or substrate 130. The barcode molecule 100 may have a variety of regions. One example region is an analyte capture domain 123. Another example region is a barcode nucleotide sequence 122. The barcode sequence 122 may be common to a plurality of the oligonucleotides 100. A barcode sequence 122 may correspond to a location on the support 130 where the oligonucleotide 100 is attached or immobilized (e.g., spatial barcode). A unique molecular identifier (UMI) may also be included as part of the barcoded nucleotide oligonucleotide. A UMI sequence may correspond to a unique molecular identifier (UMI) associated with the oligonucleotide 100. The oligonucleotide 100 may have multiple barcode sequences 122. In some examples, an oligonucleotide may have a barcode sequence that corresponds to the oligonucleotide and a barcode sequence that corresponds to the location on the support where the oligonucleotide is attached. The oligonucleotide may have other or additional regions 124 (e.g., PCR handles, cleavage domains, sequencing primer domains, etc.).

Figure 4:
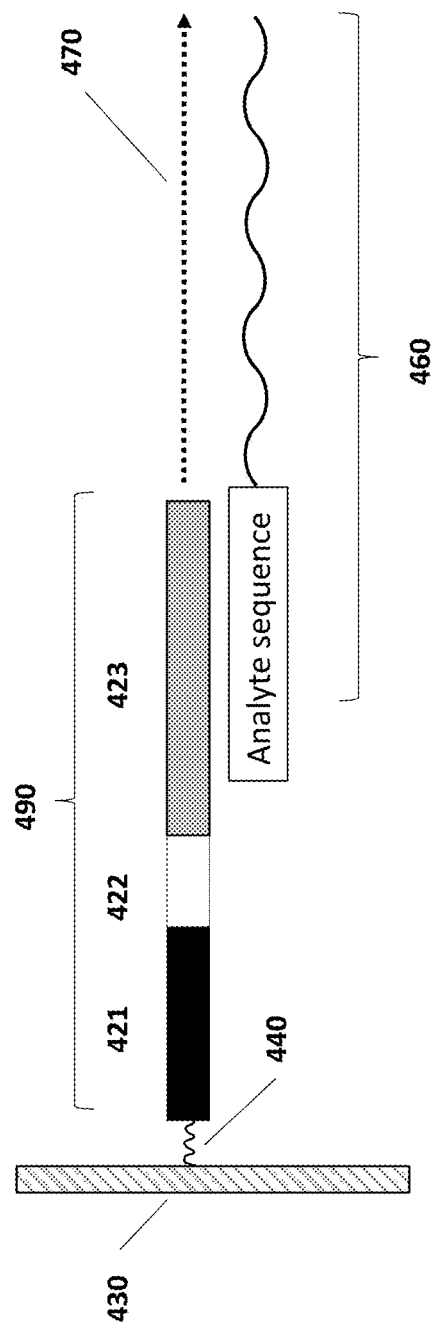
FIG. 4 is a schematic drawing (side view) that illustrates an example of a capture probe attached to a support.

In some examples, referring to FIG. 4, a barcoded oligonucleotide or capture probe 490 comprises a barcode sequence 422 corresponding to a location on a support 430 to which the oligonucleotide is attached (as illustrated in this example, the oligonucleotide 490 is attached to the support 430 via a modification or chemical moiety 440 capable of attaching to the support 430). The modification or chemical moiety 440 attached to the support can be a cleavable moiety (e.g., photocleavable, chemically cleavable, enzymatically cleavable, etc.). The illustrated oligonucleotide 490 also comprises a sequence 423 (i.e., an analyte capture sequence or capture domain) complementary to a sequence of an analyte (e.g., mRNA molecule) 460 from a cell. In some instances, sequence 423 comprises a sequence specific for an mRNA molecule. In some instances, sequence 423 comprises a poly(dT) sequence. In some instances, sequence 423 comprises a defined nucleotide sequence, a semi-random nucleotide sequence or a random nucleotide sequence. Sequence 423 is hybridized to mRNA molecule 460 (i.e., the mRNA is captured by the 423 sequence) and extended via a nucleic acid reaction (e.g., a cDNA molecule 470 is generated in a reverse transcription reaction) generating a complementary oligonucleotide comprising barcode sequence 422 (e.g., a spatial barcode sequence, or a reverse complement thereof) and a sequence of the extended nucleic acid (e.g., cDNA 470) (or a portion thereof). A functional sequence 421, such as a primer binding site for amplification and/or a sequencing related primer binding site (e.g., a sequence used for a sequencing reaction), etc. is also included in the barcoded oligonucleotide or capture probe. In some examples, barcoded nucleic acid molecules can then be optionally processed as described elsewhere herein, e.g., to amplify the molecules and/or append sequencing platform specific sequences to the fragments. Barcoded nucleic acid molecules, or derivatives generated therefrom, can then be sequenced on a suitable sequencing platform. Nucleic acid barcode molecule 490 may be attached to support 430 optionally via a releasable linkage 440 (e.g., comprising a labile bond), such as those described in WO2020/047007A2 (Appl. No. PCT/US2019/048430), WO2020/047010A2 (Appl. No. PCT/US2019/048434), WO2020/047004A3 (Appl. No. PCT/US2019/048427), and WO2020/047005A1 (PCT/US2019/048428), each of which are incorporated by reference herein in their entirety.

Figure 2:
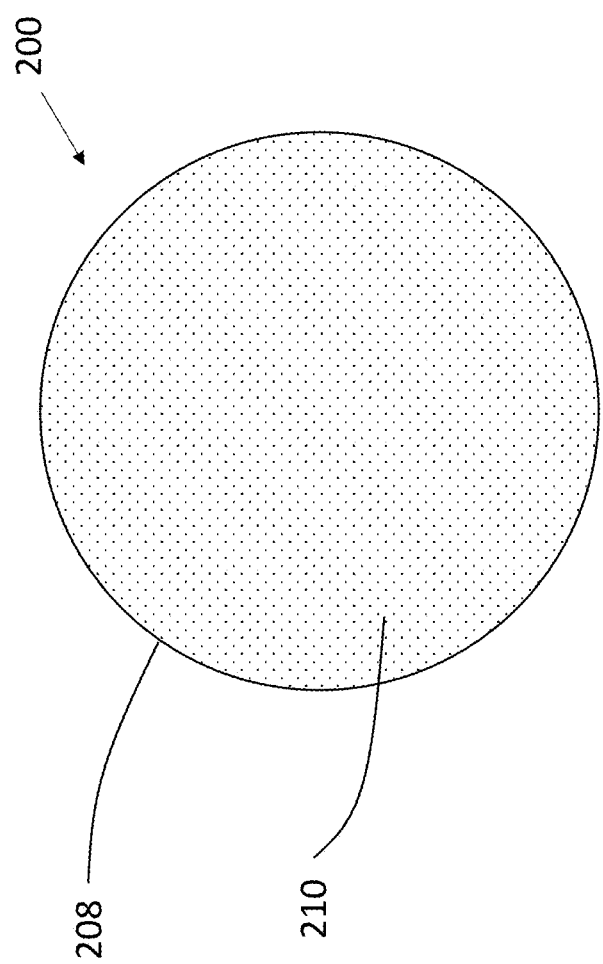
FIG. 2 is a schematic drawing (top view) that illustrates an example of a region (e.g., an array spot) on a support that contains a species of capture probe (i.e., a plurality of a species of capture probes).
Figure 3:
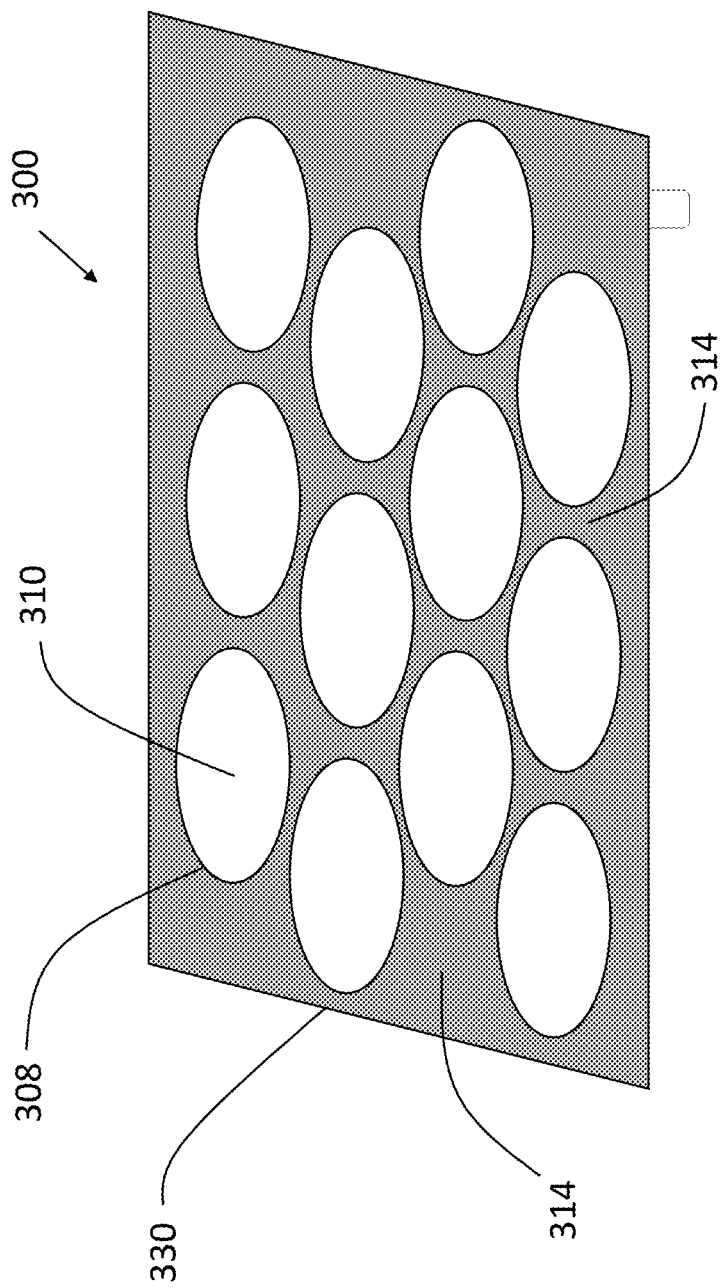
FIG. 3 is a schematic drawing (top, angular view) that illustrates an example of a region on a support with multiple species of capture probes (e.g., a spatial array).

FIG. 2 is a schematic drawing (top view) that illustrates an example region 200 of a support that contains a plurality of oligonucleotides, individual of the oligonucleotides shown in FIG. 1 and FIG. 4. Such a region, that contains an uninterrupted area of oligonucleotides attached to a support, may be referred to as a "spot," "array spot", "feature", "partition" or "demarcated region" 208. In some examples, the oligonucleotides that make up a spot are printed onto the support. In the example, each dot 210 within the demarcated region 208 represents one or a plurality of oligonucleotides attached to the support. In some examples, the oligonucleotides 210 within the demarcated region 208 may all contain the same barcode sequence that corresponds to the location on the support where the oligonucleotides are attached (e.g., spatial barcode). In some examples, the analyte capture domains may be poly(dT). In some examples, the oligonucleotides 210 within the demarcated region 208 may contain different unique molecular identifiers. In some examples, the oligonucleotides 210 within the demarcated region 208 may contain different barcode sequences that correspond to the analyte capture domain encoded by the oligonucleotide (e.g., the oligonucleotides within the demarcated region 208 may have different analyte capture domains). In some examples, the oligonucleotides 210 within the demarcated region 208 may be said to represent a species of oligonucleotides. In some examples, a species of oligonucleotides may be oligonucleotides with at least one barcode nucleotide sequence in common. In some examples, the barcode sequence in common may be a barcode sequence corresponding to a location on a support to which the oligonucleotides are attached (e.g., spatial barcode). As described below, a support may contain multiple, adjacent demarcated regions 208. In some examples, the oligonucleotides of a region may all have the same spatial barcode. In some examples, the oligonucleotides of different regions may have different spatial barcodes. In some examples, the oligonucleotides of a single region may have originated from a single oligonucleotide that was bound to a flow cell, as is described below. In some examples, the single oligonucleotide may have been amplified using "bridge-amplification" on a flow cell. In some examples of the invention disclosed herein, a single demarcated region 208, may contain at least 500, at least 1000, at least 1500, at least 2000, at least 2500, at least 3000, at least 3500, at least 4000, at least 4500, at least 5000, at least 10,000, at least 100,000, at least 250,000, at least 500,000, at least 1,000,000 at least 1,500,000, at least 2,000,000 template oligonucleotides within a distance of 0.5, 1, 5, 10, 50, 100 or 500 μm of one another on the support.

FIG. 3 is a schematic drawing (top, angular view) of a larger area of a support than illustrated in FIG. 2. FIG. 3 illustrates an example of a region of a support containing multiple of the regions 200 shown in FIG. 2. FIG. 3 may be said to illustrate an array 300 which, herein, is a region on a support 330 that contains multiple of the spots 308 that contain multiple oligonucleotides 310 attached to the support 330. Each spot region contains multiple oligonucleotides 210, as discussed for FIG. 2. The array 300 may have areas on the support to which oligonucleotides 310 are not attached. Such areas may be called intervening regions 314. Some example arrays 300 may not have intervening regions 314 and, thus, may have continuous uninterrupted areas of oligonucleotides 310 attached to the support 314. Generally, the array 300 has multiple spots 308 of oligonucleotides 310 attached to a support 330, where the spot regions 308 are interspersed with intervening regions 314.

In some examples, the oligonucleotides 310 within a single spot have at least one barcode nucleotide sequence in common (e.g., spatial barcode). In some examples, a barcode sequence in common may correspond to a location on the support 330 to which the oligonucleotides 310 are attached. In some examples, the barcode sequence corresponding to a location on the support 330 may be different for oligonucleotides 310 within different spot regions 308. In some examples, a support 330 may have at least 50, 100, 500, 1,000, 5,000, 10,000, 20,000, 30,000, 40,000 50,000, 100,000, 500,000 or 1,000,000 spot regions 308 within one mm² on the support 330.

As described, analytes released from cells may be captured by capture domains of barcoded oligonucleotides attached to the support of the array. In some examples, cells that are overlaid onto an array may be between about 10-20 μm in diameter. In some examples, a spot 308 as illustrated in FIG. 3 may be at least 1, 2, 3, 4, 5, 6, 7, 8, 9, 10, 20, 30, 40, 50, 60, 70 or 80 μm in diameter. In some examples, a cell overlaid onto such an array may be entirely within the area of a single spot or may extend beyond the area of a single spot. In some examples, a tissue overlaid onto an array that is not entirely within the area of a single spot may be overlaid onto or cover, for example, 2, 3, 4, 5, 6, 7, 8, 9 or more different adjacent spots on the surface of the array. In some embodiments, cells and tissues on a spot may represent all one cell type, or different cell types.

Cells or tissues on an array can be permeabilized, wherein analytes (e.g., mRNAs) from the cells are released from the cells, migrate to the surface of the array and are captured by specific capture domains of the barcoded oligonucleotides. In some examples, the analytes may migrate and contact spots of the array over which the cells directly lie or contact. In some examples, the analytes may not migrate and contact spots that directly underlie or that contact the cells from which the analyte originates. Instead, analytes may diffuse away from the spot most proximal to the cell that released the analyte. For example, an analyte originating and released from a cell may migrate to and contact an array spot which it directly overlays or contacts. Additionally, or alternatively, an analyte originating and released from a cell may contact one or more adjacent or even non-adjacent array spots which are not under the cell proper. As such, an analyte may diffuse away from the spot that is directly under the cell from which it originates, wherein that analyte is captured by a barcoded oligonucleotide that is not necessarily indicative of its spatial location from its original cell.

In some examples of diffusion of analytes away from the array spots that are most proximal to cells that released the analytes, oligonucleotides of an individual array spot may capture analytes released from its most proximal overlaying cell, as well as from cells that are not most proximal and do not overlay the spot.

Resolution of spatial cell analysis systems is dependent upon analytes being released from cells and captured by barcoded oligonucleotides on the substrate underneath or as proximate to the cells from which they originate as possible. In some examples of good resolution, captured analytes are associated with cells of the overlying tissue. When analytes diffuse to non-proximal spots and/or when oligonucleotides of individual spots capture analytes from more than just the cell contacting or overlying it, resolution can be decreased. Under these circumstances, captured analytes may not be confidently associated with individual cells of the overlying tissue.

In addition to migration of analytes to array spots and oligonucleotides of the spots, there are multiple computational components of spatial transcriptomics systems that are relevant, some examples of which are described below. In some examples, errors or inaccuracies that result from at least some of these computational components can also affect the data obtained from the spatial array and contribute to the increase or decrease in resolution of these systems.

In a first example, analytes captured by oligonucleotides on an array are associated with or assigned to a location on the array. Generally, a captured analyte is associated with a particular array spot on an array via the spatial barcode of the oligonucleotide to which it hybridizes. Two oligonucleotides that are part of different array spots can have different spatial barcodes. These spatial barcodes are generally incorporated into cDNAs made from captured mRNA templates (see FIG. 4), become part of the library made from the array, and are decoded when the nucleotide sequence of the library is obtained. For example, analytes are captured by the barcoded oligonucleotides and DNA libraries are made from cDNA copies of the analytes. The DNA libraries can be sequenced and from that sequence information the identity of the mRNA, its location on the spatial array via the spatial barcode, and the number of copies (e.g., gene expression level) of the mRNA via the associated unique molecular identifier can be determined by using an analysis pipeline such as the Space Ranger software (10× Genomics).

For example, the Space Ranger software analysis pipeline can take previously obtained brightfield or fluorescence microscope images of the biological sample and overlay the gene expression data from the capture mRNA for visualization in the Loupe Browser (10X Genomics). The resolution of the spatial gene expression visualization is tied to the ability of the analytes to migrate to the proximal barcoded oligonucleotide capture probes. As such, if the analytes diffuse away from the proximal capture probes, resolution can be compromised.

As such, it would be advantageous to ensure that as many analytes as possible that are released from cells are captured by the spatial analysis systems. It would also be advantageous if analytes were captured by probes located near to the cells that release the analytes (i.e., to decrease analyte diffusion, migration distance).

Oligonucleotide Capture Probe Assemblies

Disclosed herein are assemblies of oligonucleotides that provide extended and/or branched oligonucleotide capture probes for spatial array systems commonly used for spatial transcriptomics analyses. Assembly of the oligonucleotides generally relies on a first oligonucleotide probe having a nucleotide sequence to which a complementary nucleotide sequence in a second oligonucleotide probe can hybridize. The second oligonucleotide probe may also have an additional nucleotide sequence to which a complementary nucleotide sequence in a third oligonucleotide probe can hybridize. The third oligonucleotide probe may have an additional sequence to which a fourth oligonucleotide probe can hybridize, and so on. Hybridization of the first, second, third, fourth oligonucleotides, and so on, extends the length of oligonucleotide capture probes, as are found attached to supports (e.g., slides, beads) in conventional transcriptomics systems. Hybridization of the probes may also create branching of the assemblies, as described below.

In some examples, an oligonucleotide capture probe assembly may include a spatial array with oligonucleotide capture probes attached to a support, and successive "layers" of second, third and fourth oligonucleotides hybridized thereon. Here, the oligonucleotide capture probes attached to the support may be referred to as the first or base "layer" of oligonucleotides. A population of second oligonucleotides hybridized to the first layer may be referred to as the "second layer" of oligonucleotides, and so on. In some examples, the last "layer" of oligonucleotides may be referred to as the "final" layer. Layers of oligonucleotides added to but not including the base layer, and not including the oligonucleotides of the final layer, may be referred to as "intermediate" layers of oligonucleotides. For example, in an assembly where there is a base layer and 3 additional layers of oligonucleotides added to the base layer, the oligonucleotides of the second and third layers may be called oligonucleotides of the intermediate layers. In this example, the oligonucleotides of the fourth layer may be referred to as oligonucleotides of the final layer of oligonucleotides. Generally, oligonucleotides of the base layer have at least one hybridizing nucleotide sequence complementary to a hybridizing nucleotide sequence in the oligonucleotides of the second layer of oligonucleotides. The oligonucleotides of the second layer may have at least a second hybridizing nucleotide sequence complementary to a hybridizing nucleotide sequence in the oligonucleotides of the third layer, and so on. Oligonucleotides of the final layer of oligonucleotides may have only one hybridizing nucleotide sequence that is complementary to a hybridizing nucleotide sequence in the oligonucleotides of the last layer of oligonucleotides in the intermediate layers of oligonucleotides, but additional hybridizing nucleotide sequences may be present. In some examples, one or more oligonucleotides of the base, intermediate and/or final layers of oligonucleotides may also have a capture domain sequence for capturing analytes.

In some examples, the duplexes formed when a population of oligonucleotides making up a layer in an assembly hybridizes with a population of oligonucleotides making up a successive layer have similar melting temperatures or $T_m$s. In some examples, as successive layers of oligonucleotides form duplexes with prior layers to form the oligonucleotide assemblies, the $T_m$s of duplexes for successive layers decrease the farther is the layer from the base layer. For example, the $T_m$ for the duplexes formed when the base layer of oligonucleotides hybridizes with a second layer of oligonucleotides may be higher than is the $T_m$ for the duplexes formed between the second layer of oligonucleotides and the third layer of oligonucleotides, and so on.

The progressive decrease in $T_m$ for duplexes formed between layers of oligonucleotides, the farther are the duplexed layers from the base layer, is a feature that can be advantageously used when making multi-layered assemblies of oligonucleotides. In this process, an oligonucleotide assembly can be built by simultaneously adding populations of oligonucleotides that will make up multiple layers of the assembly under conditions in which hybridization can occur. By starting the assembly process at a relatively higher temperature (at a temperature around the $T_m$ for duplexes formed with the base layer) and then gradually decreasing the temperature over time, oligonucleotides can hybridize layer by layer, according to their $T_m$s (i.e., oligonucleotides don't typically form duplexes at temperatures above their $T_m$) and the successive oligonucleotide layers can be built. Alternatively, the assembly process may be performed in a stepwise manner, by adding and hybridizing oligonucleotides of one layer at a time, before the successive layer is added and hybridized.

In the oligonucleotide assemblies, there may be different arrangements of features possessed by the oligonucleotides that make up the assemblies. In some examples, oligonucleotides of the base, intermediate and final layers of an assembly may all have spatial barcodes. In an example where a location along the surface of an oligonucleotide array is described in terms of x and y coordinates, and successive layers of an oligonucleotide assembly built on the array surface are described in terms of z coordinates, oligonucleotides of an assembly may each have one or more spatial barcodes designating its x-y coordinates, and a separate spatial barcode designating its z coordinate within the assembly. In some examples, oligonucleotides of an assembly may have one or the other of a spatial barcode designating x-y coordinates and z coordinates. In some examples, oligonucleotides of one or more of the base, intermediate and final layers of an assembly may not contain spatial barcodes. Other arrangements of spatial barcodes within the oligonucleotide assemblies are contemplated.

In some examples, oligonucleotides of the base, intermediate and final layers of an assembly may all have capture domains and unique molecular identifiers (UMIs). In some examples, oligonucleotides of one or more of the base, intermediate and final layers of an assembly may not have capture domains and UMIs. In some examples, oligonucleotides of only the final layer of an assembly may have capture domains and UMIs. Other arrangements of capture domains and UMIs within the oligonucleotide assemblies are contemplated.

Figure 5:
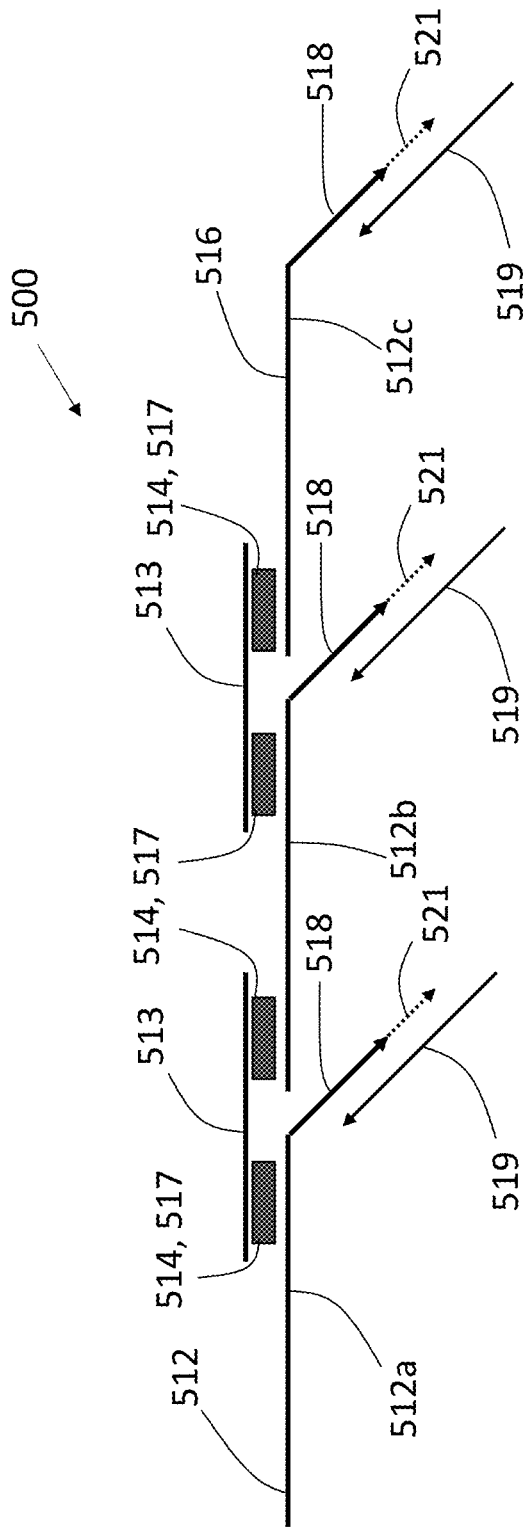
FIG. 5 is a schematic drawing illustrating an embodiment of a scaffolding arrangement of oligonucleotide capture probes.
Figure 6:
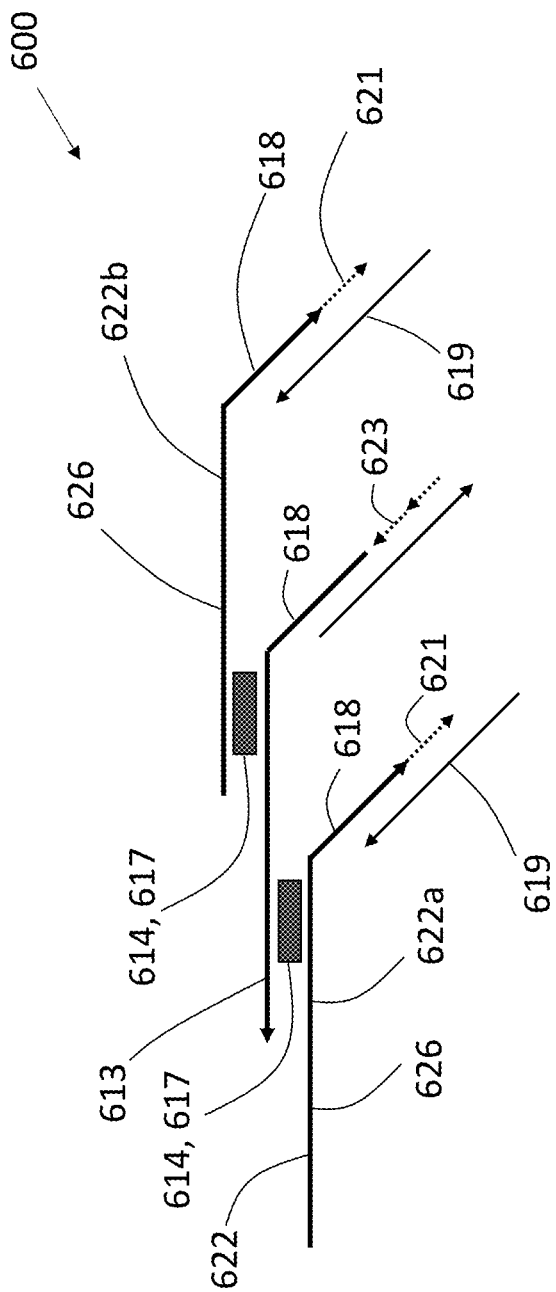
FIG. 6 is a schematic drawing illustrating another embodiment of a scaffolding arrangement of oligonucleotide capture probes.
Figure 7:
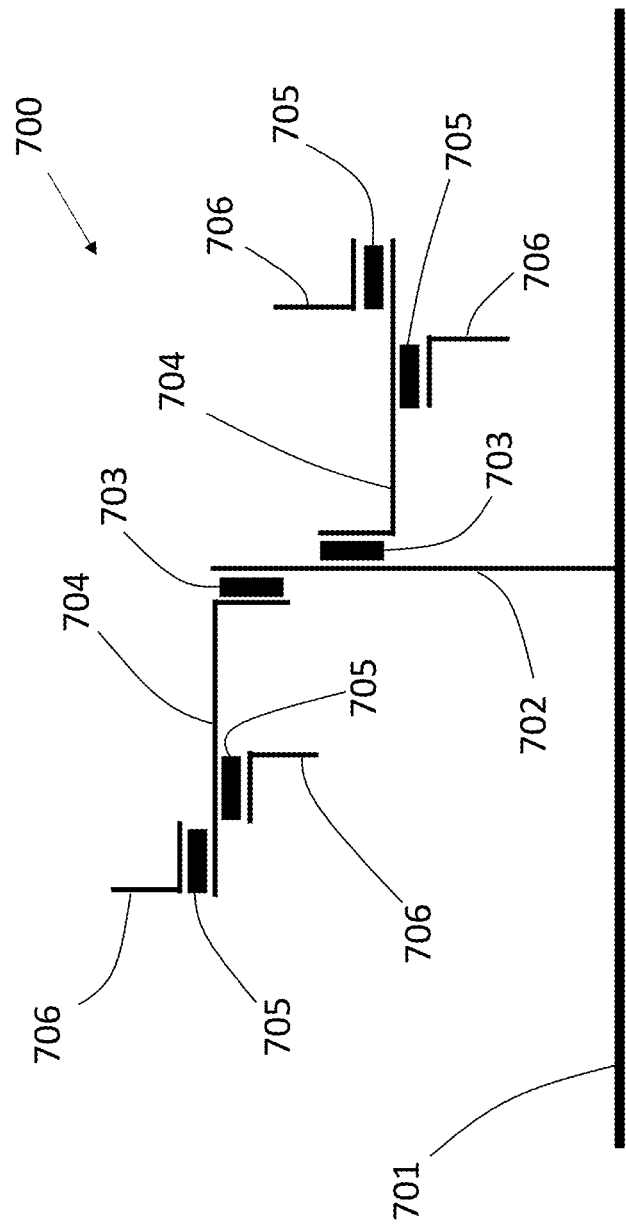
FIG. 7 illustrates a schematic of an example of a branched arrangement of assembled oligonucleotide capture probes.
Figure 8:
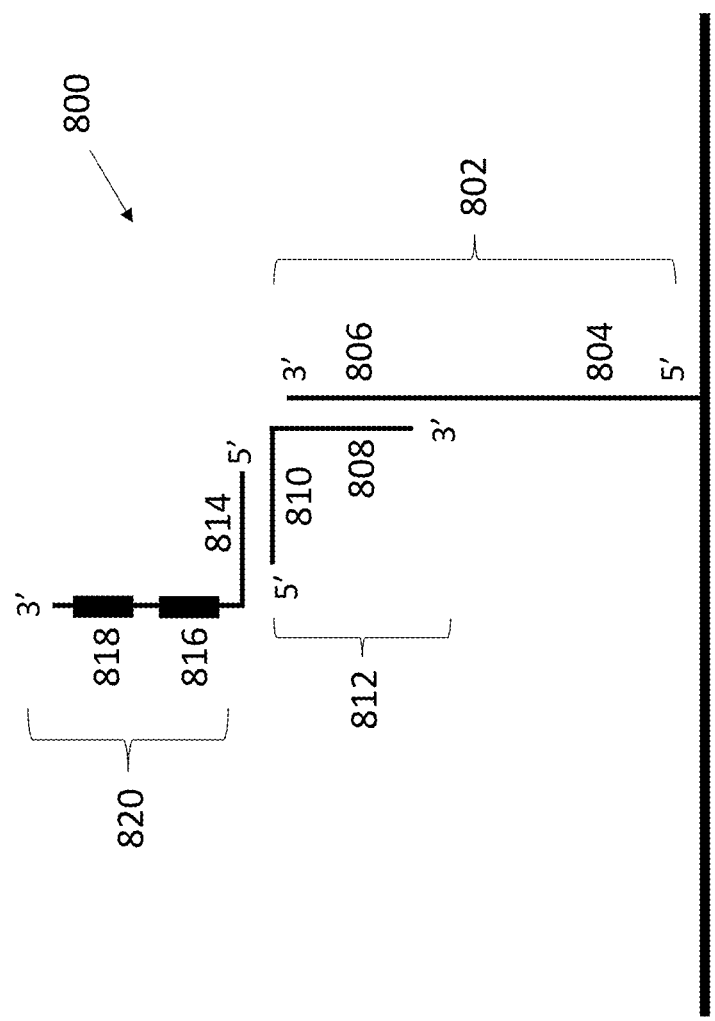
FIG. 8 illustrates a schematic of an example of a scaffolding arrangement of oligonucleotide capture probes.

In this system, when oligonucleotides that comprise a layer have a single iteration of a nucleotide sequence capable of hybridizing to oligonucleotides of a successive oligonucleotide layer, an extended oligonucleotide assembly may be built out or "extended" without branching (e.g., as in FIGS. 5, 6 and 8). In contrast, when oligonucleotides that comprise a layer have two or more iterations of a sequence or sequences to which oligonucleotides of a second layer may hybridize, the successive layer of oligonucleotides may be "branched" (e.g., as in FIG. 7).

For example, when oligonucleotides of a first layer each have two iterations of nucleotide sequences to which oligonucleotides of a second layer may hybridize, two of the second-layer oligonucleotides will hybridize to each oligonucleotide of the first layer. Conceptually, then, the total number of oligonucleotides in the second layer is twice the number of oligonucleotides in the first layer. If each oligonucleotide of the second layer also has two iterations of a sequence to which an oligonucleotide of the third layer may hybridize, the oligonucleotides in the third layer may again double. In this scenario, there is a branching or "amplification" of capture probes in the consecutive layers. In this example, the amplification is two-fold in each successive layer (e.g., from 1 to 2 to 4). Increasing the number of nucleotide sequences to which oligonucleotides in a successive layer may bind, from 2 as shown here, to 3, 4, 5, 6 or more, can result in higher levels of branching or amplification in such oligonucleotide assemblies. Increased branching of the oligonucleotide layers can increase the density of capture domains in an array.

Various nonlimiting embodiments of the oligonucleotide assemblies and the oligonucleotides that comprise the assemblies are described below.

FIG. 5 schematically illustrates a first exemplary embodiment of a spatially barcoded oligonucleotide capture probe assembly 500 that includes a branched mRNA-capturing probe 512 extending from a slide, bead or other carrier (not shown) and having a plurality of barcoded hybridization regions 514 arranged in a straight chain 516 (the box labeled 514 indicates hybridization between the single strands located on either side of the box). As illustrated, the branched mRNA-capturing probe 512 includes a plurality of segments 512a, 512b, 512c, wherein each segment includes at least a portion of an oligonucleotide sequence. Each hybridization region 514 includes at least a portion of an oligonucleotide sequence contained in segment 512a, 512b or 512c, which can be the sequence complementary to a portion of a bridging element in the embodiment shown. A bridging element 513 hybridizes to and joins the adjacent segments together and maintains the directional orientation of the segments. The bridging element 513 can include at least a portion of an oligonucleotide sequence, a polymer, a crosslinking chemical or synthetic molecule that preserves a 5' to 3' orientation of the oligonucleotide segments 512a, 512b and 512c.

A barcoded region 517, such as a spatially barcoded region, at least partially overlaps the hybridization regions 514 and can be entirely within the hybridization regions 514. An mRNA-capturing branch 518 extends from each of a plurality of hybridization regions 514 and at least part of its sequence is used to capture mRNA 519, which can be used as a template to extend the mRNA-capturing branch 518 with a polymerase to make cDNA 521. The mRNA-capturing branches 518 can include additional oligonucleotide sequences and can be joined to the oligonucleotide segments 512a, 512b and 512c by attaching the 3' ends of the mRNA-capturing branches 518 to the 5' end of the oligonucleotide segments 512a, 512b and/or 512c (as shown), or by attaching the 5' end of the mRNA-capturing branch 518 to the 3'end of the oligonucleotide segment 512a, 512b and/or 512c. In the drawing, the arrowheads represent the 3' ends of the oligonucleotide segments 512a, 512b, 512c and the mRNA-capturing branches 518, and the respective 5' ends are opposite the respective arrowheads. As used herein, the term "plurality" means "two or more" and the term each" means "each of the two or more." For example, if a hybridization region contains ten nucleotides and six of the ten nucleotides have mRNA-capturing branches extending from them, then those six nucleotides would constitute a "plurality" for purposes of this invention.

FIG. 6 schematically illustrates a second exemplary embodiment of an oligonucleotide capture probe assembly 600 of the invention. The oligonucleotide capture probe assembly 600 includes a branched mRNA-capturing probe 622 extending from a slide, bead or other carrier (not shown) and having a plurality of barcoded hybridization regions 614 arranged in a stepped (cascaded) chain 626. As illustrated, the branched mRNA-capturing probe 622 includes a plurality of stepped segments 622a, 622b, wherein each segment includes at least a portion of an oligonucleotide sequence. Each hybridization region 614 includes at least a portion of an oligonucleotide sequence contained in segment 622a or 622b, which can be sequences complementary to a bridging element in the embodiment shown. A bridging element 613 hybridizes to and joins the adjacent segments 622a and 622b together and maintains them in a stepped configuration as well as in a directional orientation of the segments. The bridging element 613 can include at least a portion of an oligonucleotide sequence, a polymer, a crosslinking chemical or synthetic molecule that preserves a 5'-3' orientation of the oligonucleotide segments 622a and 622b.

A barcoded region 617, such as a spatially barcoded region, at least partially overlaps the hybridization regions 614 and can be entirely within the hybridization regions 614. An mRNA-capturing branch 618 extends from each of a plurality of hybridization regions 614 and at least part of its sequence is used to capture mRNA 619, which can be used as a template to extend the mRNA-capturing branch 618 with a polymerase to make cDNA 621. The mRNA-capturing branches 618 can include additional oligonucleotide sequences and can be joined to the oligonucleotide segments 622a and 622b by attaching the 3' ends of the mRNA-capturing branches 618 to the 5' end of the oligonucleotide segments 622a and 622b (as shown), or by attaching the 5' end of the mRNA-capturing branch 618 to the 3'end of the oligonucleotide segment 622a and 622b. In the drawing, the arrowheads represent the 3' ends of the oligonucleotide segments 622a and 622b and the mRNA-capturing branches 618, and the respective 5' ends are opposite the respective arrowheads. The splint oligonucleotide in the bridging element 613 can include a 5' capture sequence 618' in the capturing branch 618, which can be used to capture targeted mRNA's, and which can be extended in the 5' direction through ligation of degenerated oligonucleotides, for example.

During use, the spatially barcoded oligonucleotide capture probe assembly 500, 600 is applied to a microscopic slide, such as a spatial gene expression slide. Alternatively, a base layer of oligonucleotides is attached to the slide and the successive layers are built through hybridization. Building of the oligonucleotide assemblies occurs before a tissue section has been applied to the surface of the spatial array.

Sections of biological tissue are arranged on the slide. The sections of tissue have mRNA molecules both at the tissue surfaces and the tissue interior. When the tissue sections are permeabilized, the barcoded hybridization regions 514, 614 of the branched mRNA-capturing probe 512, 612 or 522, 622 contact the adjacent surface of each tissue section and capture mRNA molecules from that tissue surface. The mRNA-capturing branches 518, 618 which can also be barcoded, extend into the interior of each tissue section and capture mRNA molecules from the interior. When the tissue sections are removed from the slide and the slide is imaged, the image will reflect mRNA molecules both at the tissue surface and the tissue interior. Because the tissue interior constitutes most of the tissue section, the resulting image can more accurately reflect the types of mRNA that exist in the tissue section and may not exist at the surface. This can result in better detection of diseases that are represented by RNA defects, including without limitation heart disease, some cancers, stroke, myotonic dystrophy, some neurogenerative diseases, and others.

Physical Characteristics of the Oligonucleotide Capture Probes

The oligonucleotide capture probes can be characterized both in terms of physical characteristics and chemistry. Physical characteristics are important in order to ensure adequate penetration of the mRNA-capturing branches into the interior of the permeabilized biological tissue. The length of a biological molecular chain can be characterized in terms of nucleotides or base units for a single stranded RNA or double stranded DNA (with one nucleotide=one base unit), or base pairs for a double stranded DNA, and the length of a mRNA-capturing branches can be similarly characterized.

The length of a base pair for a double-stranded DNA molecule is about 3.4 angstroms. Permeabilized tissue sections typically have a thickness of about 2 microns to about 20 microns, more commonly about 5 microns to about 15 microns. Preferably, tissue sections are approximately 10 microns thick. For a DNA-based mRNA capture branch to completely pass through a typical biological tissue section would therefore require a branch length of about 5880 base pairs for a 2-micron tissue section, about 14,700 base pairs for a 5-micron tissue section, about 44, 100 base pairs for a 15-micron tissue section, and about 58,800 base pairs for a 20-micron tissue section. The lengths of single-stranded RNA vary more widely, often between about 1500 and about 4500 nucleotides per micron depending on the type of RNA. Such long branches present difficulties in synthesis and can result in steric hindrance. Therefore, optimal performance of the oligonucleotide capture probe typically results using mRNA-capturing branches that probe into the tissue sections but do not necessarily pass through all of the thickness of the tissue sections.

Due to limitations in synthesis and availability, the oligonucleotide capture probe may have an overall chain length of about 20 to about 20,000 nucleotides, or about 100 to about 15,000 nucleotides, or about 1000 to about 8000 nucleotides. Thus, for a mRNA-capturing branch to penetrate completely through the permeabilized biological tissue, the length of the mRNA-capturing branches would have to be large relative to the chain length of the oligonucleotide capture probe. This can be impractical because excessively long branches might fold or curl on or near the tissue surface instead of accessing the interior of the tissue. Moreover, excessively long branches might entangle and/or hinder each other and obstruct contact between the tissue surface and the barcoded hybridization regions of the oligonucleotide capture probe.

For these reasons, the mRNA-capturing branches should be designed to penetrate as far as possible into the biological tissue while avoiding the problems associated with excessive length. The mRNA-capturing branches may have lengths of at least about 5 nucleotides, or at least about 10 nucleotides, or at least about 20 nucleotides, or at least about 50 nucleotides, or at least about 100 nucleotides, or at least about 250 nucleotides, or at least about 500 nucleotides, or at least about 750 nucleotides, or at least about 1000 nucleotides. The optimal length may vary depending on the overall chemistry of the oligonucleotide capture probe, the relative rigidity of the mRNA-capturing branches, the type and thickness of the permeabilized biological tissue, and other factors.

The oligonucleotide capture probe includes a plurality of hybridized regions arranged in a chain. The hybridized regions are suitably barcoded and are suitably spatially barcoded. In one embodiment, it may be desirable to include as many as possible hybridized regions per the overall chain length of the oligonucleotide capture probe. This embodiment would enable a high number of mRNA-capturing branches extending from the hybridized regions, especially where an mRNA-capturing branch extends from each of the hybridized regions. In this embodiment, the hybridized regions of the oligonucleotide capture probe may have individual lengths of about 5 to about 2000 nucleotides, or about 10 to about 1000 nucleotides, or about 20 to about 500 nucleotides, or about 25 to about 100 nucleotides. In another embodiment, it may be desirable for the hybridized regions to have lengths like or exceeding the lengths of the mRNA-capturing branches, so that the mRNA-capturing branches do not significantly hinder contact between the hybridized regions and the surfaces of the permeabilized tissue sections. In this embodiment, the hybridized regions may have lengths of at least about ten nucleotides, or at least about 20 nucleotides, or at least about 50 nucleotides, or at least about 100 nucleotides, or at least about 250 nucleotides, or at least about 500 nucleotides, or at least about 750 nucleotides, or at least about 1000 nucleotides.

Chemistry of the Oligonucleotide Capture Probe

Referring to FIGS. 5 and 6, the exemplary spatially barcoded oligonucleotide capture probe 500 or 600 includes a branched mRNA-capturing probe 512 or 622 having a plurality of barcoded hybridization regions 514 arranged in a straight chain 516 or stepped chain 626. A plurality of mRNA-capturing branches 518, 618 extend from the hybridization regions 514, 614. The hybridization regions 514, 614 arranged in the chain 516 or 626 serve as capture domains for target mRNA present on the adjacent surface of the tissue sections. Each capture domain can be an oligonucleotide, a polypeptide, a small molecule, or any combination thereof, that binds, captures and/or detects a target mRNA.

Chemistry of Capture Regions

Each capture domain can be a functional nucleic acid sequence configured to interact with the target mRNA molecules. The functional sequence can include a poly(T) sequence, which poly(T) sequences are configured to interact with the mRNA molecules via the poly(A) tail of an mRNA transcript.

Capture domains can include ribonucleotides and/or deoxyribonucleotides as well as synthetic nucleotide residues that can participate in Watson-Crick type or analogous base pair interactions. The capture domains can prime a reverse transcription reaction to generate cDNA that is complementary to the captured mRNA molecules.

A capture domain can be located at the end of the capture probe and can include a free 3' end that can be extended, e.g., by template dependent polymerization, to form an extended capture probe. In some embodiments, the capture domain includes a nucleotide sequence that is capable of hybridizing to mRNA present in the cells of the biological tissue contacted with the array. The capture domain can be selected or designed to bind selectively or specifically to a target mRNA by way of hybridization to the mRNA poly(A) tail. Thus, the capture domain can include a poly(T) DNA oligonucleotide, e.g., a series of consecutive deoxythymidine residues linked by phosphodiester bonds, which is capable of hybridizing to the poly(A) tail of mRNA. The capture domain can include nucleotides that are functionally or structurally analogous to a poly(T) tail, for example, a poly(U) oligonucleotide or an oligonucleotide including deoxythymidine analogues. The capture domain can have a sequence that is capable of binding to mRNA. For example, the capture domain can include a nucleic acid sequence (e.g., a poly(T) sequence) capable of binding to a poly(A) tail of an mRNA. In some embodiments, a homopolymer sequence is added to an mRNA molecule using a terminal transferase enzyme in order to produce a molecule having a poly(A) or poly(T) sequence. For example, a poly(A) sequence can be added to an mRNA, thereby making the mRNA capable of capture by a poly(T) capture domain.

In some embodiments, random sequences, e.g., random hexamers or similar sequences, can be used to form all or a part of the capture domain. Example, random sequences can be used in conjunction with poly(T) (or poly(T) analogue) sequences. Thus, where a capture domain includes a poly(T) (or a "poly(T)-like") oligonucleotide, it can also include a random oligonucleotide sequence (e.g., "poly(T)-random sequence" probe). This can, for example, be located at 5' or 3' of the poly(T) sequence, e.g., at the 3' end of the capture domain. The poly(T)-random sequence probe can facilitate the capture of the mRNA poly(A) tail. In some embodiments, the capture domain can be an entirely random sequence. In some embodiments, degenerate capture domains can be used.

In some embodiments, a pool of two or more capture probes form a mixture, where the capture domain of one or more capture probes includes a poly(T) sequence and the capture domain of one or more capture probes includes random, semi-random or non-random sequences. In some embodiments, a pool of two or more capture probes form a mixture where the capture domain of one or more capture probes includes a poly(T)-like sequence and the capture domain of one or more capture probes includes random, semi-random or non-random sequences. In some embodiments, probes with degenerate capture domains can be added to any of the preceding combinations listed herein. In some embodiments, probes with degenerate capture domains can be substituted for one of the probes in each of the pairs described herein.

The capture domain can be based on a gene sequence, a motif sequence or common/conserved sequence that it is designed to capture (i.e., a sequence-specific capture domain). Thus, the capture domain can be capable of binding selectively to a desired sub-type or subset of nucleic acid, for example a type or subset of mRNA. In some embodiments, a capture domain includes an "anchor" or "anchoring sequence," which is a sequence of nucleotides designed to ensure that the capture domain hybridizes to the intended mRNA. The anchor sequence can include a sequence of nucleotides, including a 1-mer, 2-mer, 3-mer or longer sequence. The sequence can be random. For example, a capture domain including a poly(T) sequence can be designed to capture an mRNA. An anchoring sequence can include a random 3-mer (e.g., GGG) that helps ensure that the poly(T) capture domain hybridizes to an mRNA. In some embodiments, an anchoring sequence can be VN, N, or NN. Alternatively, the sequence can be designed using a specific sequence of nucleotides. In some embodiments, the anchor sequence is at the 3' end of the capture domain. In some embodiments, the anchor sequence is at the 5' end of the capture domain.

Referring to FIG. 5, the mRNA-capturing branches 518 extend from the hybridization regions 514, can be barcoded, and can serve the same chemical purpose of the capture domains that define the hybridization regions. The primary difference is that the hybridization regions 514 capture mRNA from the adjacent surface of the tissue section, whereas the mRNA-capturing branches 518 capture mRNA that is present in the interior of the tissue section.

In the exemplary embodiments shown in FIGS. 5 and 6, the hybridization regions 514, 614 and the mRNA-capturing branches 518, 618 can each be formed of the same barcoded mRNA-capturing oligonucleotide, which can be a bar-coded oligo-dT oligonucleotide.

Barcode Chemistry

Referring to FIGS. 5 and 6, each hybridized region 514, 614 and each mRNA-capturing branch 518, 618 may include a barcode 517, 617, which can suitably be a spatial barcode. The mRNA-capturing probe 512 or 622 can thus include several spatial barcodes, for example, barcodes corresponding to each of the hybridized regions 514, 614 and each of the mRNA-capturing branches 518, 618. A "spatial barcode" is a contiguous nucleic acid segment or two or more non-contiguous nucleic acid segments that function as a label or identifier that conveys or can convey spatial information. In some embodiments, the spatial barcodes are associated with locations within the array or tissue section.

A spatial barcode can function both as a spatial barcode and as a unique molecular identifier (UMI), associated with a capture probe or capture domain. Spatial barcodes can have a variety of different formats. For example, spatial barcodes can include polynucleotide spatial barcodes, random nucleic acid and/or amino acid sequences, and synthetic nucleic acid and/or amino acid sequences. In some embodiments, a spatial barcode is attached to an mRNA before, during, and/or after sequencing. The spatial barcode can allow for identification and/or quantification of individual sequencing-reads. The spatial barcode can be a fluorescent barcode for which fluorescently labeled oligonucleotide probes hybridize to the spatial barcode. The spatial barcode can be a nucleic acid sequence that does not substantially hybridize to mRNA molecules in a biological tissue. In some embodiments, the spatial barcode has less than 80% sequence identity (e.g., less than 70%, 60%, 50%, or less than 40% sequence identity) to the nucleic acid sequences across a substantial part (e.g., 80% or more) of the mRNA molecules in the biological tissue. The spatial barcode sequences can include from about 5 to about 20 or more nucleotides within the sequence of the mRNA-capturing probe. For example, the length of a spatial barcode sequence can be about 6, 7, 8, 9, 10, 11, 12, 13, 14, 15, 16, 17, 18, 19, 20 nucleotides or longer. In some embodiments, the length of a spatial barcode sequence can be at least about 6, 7, 8, 9, 10, 11, 12, 13, 14, 15, 16, 17, 18, 19, 20 nucleotides or longer, or at most about 6, 7, 8, 9, 10, 11, 12, 13, 14, 15, 16, 17, 18, 19, 20 nucleotides or shorter. However, while a spatial barcode could also function as a UMI, a UMI could also be a separate sequence found on the capture probe. As such, a capture probe could have both a spatial barcode and a UMI, which are of different sequence.

These nucleotides can be completely contiguous, e.g., in a single stretch of adjacent nucleotides, or they can be separated into two or more subsequences that are separated by 1 or more nucleotides. Separated spatial barcode subsequences can be from about 4 to about 16 nucleotides in length. In some embodiments, the spatial barcode subsequence can be about 4, 5, 6, 7, 8, 9, 10, 11, 12, 13, 14, 15, 16 nucleotides or longer, or at least about 4, 5, 6, 7, 8, 9, 10, 11, 12, 13, 14, 15, 16 nucleotides or longer, at most about 4, 5, 6, 7, 8, 9, 10, 11, 12, 13, 14, 15, 16 nucleotides or shorter. For multiple capture probes that are attached to a common array feature, the one or more spatial barcode sequences of the multiple capture probes can include sequences that are the same for all capture probes coupled to the feature, and/or sequences that are different across all capture probes coupled to the feature.

Synthesis of the Oligonucleotide Capture Probe Assembly

Referring to FIGS. 5 and 6, a key to the spatially barcoded oligonucleotide capture probe assembly 500 or 600 is the branched mRNA-capturing probe 512 or 622 having a plurality of hybridization regions 514 arranged in a straight 516 or stepped chain 626, and an mRNA-capturing branch 518, 618 extending from each hybridization region 514, 614. The dashed lines 521, 621 in the mRNA-capturing branches 518, 618 represent a typical reverse transcription product, namely cDNA. The dashed lines 623 with arrows (FIG. 6) reflect the use of chemical ligation to attach and/or lengthen the mRNA-capturing branches. The mRNA-capturing branches can be attached to the barcoded hybridization regions using chemical ligation and can also be barcoded. Chemical ligation connects two oligonucleotides, in this case a capture domain and an mRNA-capturing branch, by covalent bonding using a third oligonucleotide called a template strand, typically in the presence of a condensing reagent. The two oligonucleotides are assembled on the template in opposite directions by forming antiparallel and parallel duplexes simultaneously, followed by coupling with a condensing reagent such as N-cyanoimidazole under mild conditions. The ligation reaction results in the formation of 3' to 3' or 5' to 5' ester bonds between the two oligonucleotides.

Specific examples of chemical ligation are described in detail in U.S. Pat. No. 7,264,929, the disclosure of which is incorporated by reference. Chemical ligation has commonly been used to form longer chain oligonucleotides including, for example, longer chain cDNA molecules. The present invention applies the chemical ligation techniques to synthesize branched mRNA-capturing probes useful in spatial transcriptomics, by attaching the branched mRNA-capturing domains to the capture domains of straight-chain oligonucleotides such as those used in conventional reverse transcription primers. The capture domains in the main chain and the mRNA-capturing branches can be barcoded using conventional techniques. The barcoding can be accomplished before or after the chemical ligation of the mRNA-capturing branches to the capture domains in the primary chain.

Branched Oligonucleotide Assemblies

In other examples, the oligonucleotide capture probe assemblies can be designed to increase the density of capture domains within an area. FIG. 7 is a schematic representation of such an embodiment. FIG. 7 illustrates an example oligonucleotide capture probe assembly 700. In the assembly 700, a first oligonucleotide 702 is attached to a support 701. The support 700 may be part of a spatial array.

The first oligonucleotide 702 contains at least two nucleotide sequences 703 that are complementary to sequences in a second oligonucleotide 704 (note that rectangles designated as 703 represent hybridization between 702 and 704). Two second oligonucleotides 704 hybridize to the single first oligonucleotide 702 via the nucleotide sequences 703. Each of the second oligonucleotides 704 contain two nucleotide sequences 705 that are complementary to sequences in a third oligonucleotide 706 (note that the rectangles designated as 705 represent hybridization between 704 and 706). Two third oligonucleotides 706 hybridize to each second oligonucleotide 704 via the nucleotide sequences 705.

This embodiment demonstrates how increasing, in an oligonucleotide, the number of nucleotide sequences to which a second oligonucleotide can hybridize, "amplifies" the number of oligonucleotides and, in some examples, the number of capture domains in the oligonucleotides, within an area or volume. In the example here, two second oligonucleotides hybridize to a single first oligonucleotide. In the example, two third oligonucleotides hybridize to each of the two illustrated second oligonucleotides. Therefore, a single first oligonucleotide is "amplified" to two second oligonucleotides, which are amplified to four third oligonucleotides (1+2+4). One can alter this amplification and the density of oligonucleotides within an assembly by changing the number of hybridizing nucleotide sequences within oligonucleotides of the system. The invention contemplates 1, 2, 3, 4, 5, 6 or more hybridizing nucleotide sequences within oligonucleotides used to form the oligonucleotide assemblies described herein. By increasing the number of oligonucleotides in the assembly, the number of capture domains can also be increased. For example, oligonucleotide 706 can each comprise a capture domain in the unhybridized region. In viewing FIG. 7, one can see from one oligonucleotide affixed to the array substrate (702) there are found 4 potential capture domains, or free ends of the oligonucleotide 706 that are available to capture target analytes.

Duplex Melting Temperatures in Oligonucleotide Assemblies

In another feature of the disclosed oligonucleotide assemblies, the nucleotide sequences within oligonucleotides of the assemblies that hybridize to other oligonucleotides (i.e., hybridizing nucleotide sequences), thus building the successive "layers" of the assemblies, may be designed to have different melting temperatures or $T_m$'s. In some examples, the $T_m$'s for hybridization of the oligonucleotides of one layer to oligonucleotides of a successive layer may be the same. This feature provides for formation of duplexes between all the oligonucleotides of the two intersecting layers at the same temperature and at the same time when the oligonucleotide assemblies are built.

In addition to the feature of duplexes between layers of oligonucleotides having about the same $T_m$, the oligonucleotides of an assembly may be designed such that $T_m$'s of duplexes between two layers decrease the farther from the base layer the duplexes are located. For example, the $T_m$ for duplexes formed between the second and third layers of oligonucleotides in an assembly may be higher than the $T_m$ for duplexes formed between the third and fourth layer of oligonucleotides in the assembly. Similarly, the $T_m$ for duplexes formed between the third and fourth layers of oligonucleotides in an assembly may be higher than the $T_m$ for duplexes formed between the fourth and fifth layers of oligonucleotides in the assembly, and so on.

FIG. 8 illustrates an example of this. First, an array with a plurality of first probes and a biological sample disposed on the array is provided. The plurality of first probes is affixed to the array surface and a first probe 802 of the plurality of first probes includes a first hybridization sequence 806. Second, the array is contacted with a biological sample, a plurality of second probes, and a plurality of third probes. The second probe 812 of the plurality of second probes comprises in a 3' to a 5' direction: (i) a second hybridization sequence 808 that specifically binds to the first hybridization sequence 806 in the first probe at a temperature that is about or less than a first melting temperature, and (ii) a third hybridization sequence 810. A third probe 820 of the plurality of third probes comprises in a 5' to a 3' direction: (i) a fourth hybridization sequence 814 that specifically binds to the third hybridization sequence 810 in the second probe at a temperature that is about or less than a second melting temperature, where the first melting temperature is higher than the second melting temperature, (ii) a spatial barcode 816, and (iii) a capture domain 818 that specifically binds to a target analyte. A first probe of the plurality of first probes may comprise a first probe spatial barcode 804.

In some embodiments, by placing the biological sample with array and the first, second, and third probes, and decreasing the temperature from a temperature of about or less than the first melting temperature to a temperature of about or less than the second melting temperature, the first, second, and third probes assemble to create an organized structure that 'invades' the biological sample in an organized fashion in a direction perpendicular from the two-dimensional surface of the array (z-direction), while remaining affixed to the array. In other embodiments, the structures are built on the array, following a pattern of decreasing temperature as described above, prior to placing the biological sample on the array.

Additional Embodiments

Regarding the features of the oligonucleotide assemblies described herein, the methods and systems may include the use of an array (e.g., any of the exemplary arrays described herein), where the array has a plurality of first probes affixed (i.e., attached) to the array (i.e. reversibly or non-reversibly).

A first probe of the plurality of first probes can include a first hybridization sequence.

The first hybridization sequence can have a total of about 5 nucleotides to about 100 nucleotides, about 5 nucleotides to about 90 nucleotides, about 5 nucleotides to about 80 nucleotides, about 5 nucleotides to about 70 nucleotides, about 5 nucleotides to about 60 nucleotides, about 5 nucleotides to about 50 nucleotides, about 5 nucleotides to about 40 nucleotides, about 5 nucleotides to about 30 nucleotides, about 5 nucleotides to about 25 nucleotides, about 5 nucleotides to about 20 nucleotides, about 5 nucleotides to about 15 nucleotides, about 5 nucleotides to about 10 nucleotides, about 10 nucleotides to about 100 nucleotides, about 10 nucleotides to about 90 nucleotides, about 10 nucleotides to about 80 nucleotides, about 10 nucleotides to about 70 nucleotides, about 10 nucleotides to about 60 nucleotides, about 10 nucleotides to about 50 nucleotides, about 10 nucleotides to about 40 nucleotides, about 10 nucleotides to about 30 nucleotides, about 10 nucleotides to about 25 nucleotides, about 10 nucleotides to about 20 nucleotides, about 10 nucleotides to about 15 nucleotides, about 15 nucleotides to about 100 nucleotides, about 15 nucleotides to about 90 nucleotides, about 15 nucleotides to about 80 nucleotides, about 15 nucleotides to about 70 nucleotides, about 15 nucleotides to about 60 nucleotides, about 15 nucleotides to about 50 nucleotides, about 15 nucleotides to about 40 nucleotides, about 15 nucleotides to about 30 nucleotides, about 15 nucleotides to about 25 nucleotides, about 15 nucleotides to about 20 nucleotides, about 20 nucleotides to about 100 nucleotides, about 20 nucleotides to about 90 nucleotides, about 20 nucleotides to about 80 nucleotides, about 20 nucleotides to about 70 nucleotides, about 20 nucleotides to about 60 nucleotides, about 20 nucleotides to about 50 nucleotides, about 20 nucleotides to about 40 nucleotides, about 20 nucleotides to about 30 nucleotides, about 20 nucleotides to about 25 nucleotides, about 25 nucleotides to about 100 nucleotides, about 25 nucleotides to about 90 nucleotides, about 25 nucleotides to about 80 nucleotides, about 25 nucleotides to about 70 nucleotides, about 25 nucleotides to about 60 nucleotides, about 25 nucleotides to about 50 nucleotides, about 25 nucleotides to about 40 nucleotides, about 25 nucleotides to about 30 nucleotides, about 30 nucleotides to about 100 nucleotides, about 30 nucleotides to about 90 nucleotides, about 30 nucleotides to about 80 nucleotides, about 30 nucleotides to about 70 nucleotides, about 30 nucleotides to about 60 nucleotides, about 30 nucleotides to about 50 nucleotides, about 30 nucleotides to about 40 nucleotides, about 40 nucleotides to about 100 nucleotides, about 40 nucleotides to about 90 nucleotides, about 40 nucleotides to about 80 nucleotides, about 40 nucleotides to about 70 nucleotides, about 40 nucleotides to about 60 nucleotides, about 40 nucleotides to about 50 nucleotides, about 50 nucleotides to about 100 nucleotides, about 50 nucleotides to about 90 nucleotides, about 50 nucleotides to about 80 nucleotides, about 50 nucleotides to about 70 nucleotides, about 50 nucleotides to about 60 nucleotides, about 60 nucleotides to about 100 nucleotides, about 60 nucleotides to about 90 nucleotides, about 60 nucleotides to about 80 nucleotides, about 60 nucleotides to about 70 nucleotides, about 70 nucleotides to about 100 nucleotides, about 70 nucleotides to about 90 nucleotides, about 70 nucleotides to about 80 nucleotides, about 80 nucleotides to about 100 nucleotides, about 80 nucleotides to about 90 nucleotides, or about 90 nucleotides to about 100 nucleotides. Second, third, fourth, fifth hybridization sequences, and so on, may have similar properties.

In some embodiments of any of the methods described herein, the first probe can also include a spatial barcode positioned adjacent (e.g., positioned 5') to the first hybridization sequence.

The first probe may also include a capture domain. In some examples, the capture domain can include a poly(T) sequence.

In some embodiments of any of the methods described herein, the first probe can also include a cleavage domain (e.g., any of the exemplary cleavage domains described herein) positioned adjacent (e.g., positioned 5') to the spatial barcode, if the spatial barcode is present on the first probe. In some embodiments, the cleavage domain can be a disulfide bond that is cleaved by inducing reducing conditions.

The array to which the first probes are affixed may have any of the characteristics of any of the arrays described herein. For example, the plurality of first probes can be printed on, or attached to, the array in designated spots, wherein the spots are separated from each other by a distance of about 20 pm, about 30 pm, about 40 pm, about 50 pm, about 60 pm, about 70 pm, about 80 pm, about 90 pm, about 100 pm, about 125 pm, about 150 pm, about 175 pm, about 200 pm, from the center of one spot to the center of the next spot.

In some embodiments of any of the methods described herein, the array includes a slide. In some embodiments, the array can be a bead array (e.g., any of the exemplary bead arrays described herein).

A second probe of the plurality of second probes comprises (e.g., in a 3' to a 5' direction): (i) a second hybridization sequence that specifically binds to the first hybridization sequence at a temperature that is about or less than a first melting temperature, and (ii) a third hybridization sequence. The second probe may comprise an analyte capture domain.

A third probe of the plurality of third probes comprises (e.g., in a 5' to a 3' direction): (i) a fourth hybridization sequence that specifically binds to the third hybridization sequence at a temperature that is about or less than a second melting temperature, where the first melting temperature is higher than the second melting temperature, (ii) a spatial barcode, and (iii) a capture domain that specifically binds to a target analyte (e.g., any of the exemplary capture domains described herein binding any of the exemplary target analytes described herein).

The first hybridization sequence and the second hybridization sequence specifically bind to each other at a temperature that is about or less than the first melting temperature. In some embodiments, the first melting temperature is about 55° C. to about 65° C., about 55° C. to about 64° C., about 55° C. to about 63° C., about 55° C. to about 62° C., about 55° C. to about 61° C., about 55° C. to about 60° C., about 55° C. to about 59° C., about 55° C. to about 58° C., about 55° C. to about 57° C., about 56° C. to about 65° C., about 56° C. to about 64° C., about 56° C. to about 63° C., about 56° C. to about 62° C., about 56° C. to about 61° C., about 56° C. to about 60° C., about 56° C. to about 59° C., about 56° C. to about 58° C., about 57° C. to about 65° C., about 57° C. to about 64° C., about 57° C. to about 63° C., about 57° C. to about 62° C., about 57° C. to about 61° C., about 57° C. to about 60° C., about 57° C. to about 59° C., about 58° C. to about 65° C., about 58° C. to about 64° C., about 58° C. to about 63° C., about 58° C. to about 62° C., about 58° C. to about 61° C., about 58° C. to about 60° C., about 59° C. to about 65° C., about 59° C. to about 64° C., about 59° C. to about 63° C., about 59° C. to about 62° C., about 59° C. to about 61° C., about 60° C. to about 65° C., about 60° C. to about 64° C., about 60° C. to about 63° C., about 60° C. to about 62° C., about 61° C. to about 65° C., about 61° C. to about 64° C., about 61° C. to about 63° C., about 62° C. to about 65° C., about 62° C. to about 64° C., or about 63° C. to about 65° C. In some embodiments, the first melting temperature can be about 58° C. to about 62° C.

The third hybridization sequence of the second probe and the fourth hybridization sequence of the third probe specifically bind to each other at a temperature that is about or less than the second melting temperature. In some embodiments, the second melting temperature is about 45° C. to about 55° C., about 45° C. to about 54° C., about 45° C. to about 53° C., about 45° C. to about 52° C., about 45° C. to about 51° C., about 45° C. to about 50° C., about 45° C. to about 49° C., about 45° C. to about 48° C., about 45° C. to about 47° C., about 46° C. to about 55° C., about 46° C. to about 54° C., about 46° C. to about 53° C., about 46° C. to about 52° C., about 46° C. to about 51° C., about 46° C. to about 50° C., about 46° C. to about 49° C., about 46° C. to about 48° C., about 47° C. to about 55° C., about 47° C. to about 54° C., about 47° C. to about 53° C., about 47° C. to about 52° C., about 47° C. to about 51° C., about 47° C. to about 50° C., about 47° C. to about 49° C., about 48° C. to about 55° C., about 48° C. to about 54° C., about 48° C. to about 53° C., about 48° C. to about 52° C., about 48° C. to about 51° C., about 48° C. to about 50° C., about 49° C. to about 55° C., about 49° C. to about 54° C., about 49° C. to about 53° C., about 49° C. to about 52° C., about 49° C. to about 51° C., about 50° C. to about 55° C., about 50° C. to about 54° C., about 50° C. to about 53° C., about 50° C. to about 52° C., about 51° C. to about 55° C., about 51° C. to about 54° C., about 51° C. to about 53° C., about 52° C. to about 55° C., about 52° C. to about 54° C., or about 53° C. to about 55° C. In some embodiments, the second melting temperature is about 48° C. to about 52° C.

In some embodiments of any of these methods, contacting of the probes to build an oligonucleotide assembly includes decreasing the temperature from a temperature of about or less than the first melting temperature to a temperature of about or less than the second melting temperature. The decreasing of the temperature from a temperature of about or less than the first melting temperature to a temperature of about or less than the second melting temperature results in the first hybridization sequence of the first probe specifically binding to the second hybridization sequence of the second probe, and the third hybridization sequence of the second probe specifically binding to the fourth hybridization sequence of the third probe. Additional probes can be hybridized using this strategy.

Additional probes and corresponding hybridization sequences can be used in a similar fashion. Additional hybridization sequences in additional probes may have similarly decreasing binding/melting temperatures.

Some embodiments of any of the methods described herein include disposing a biological sample (e.g., any biological sample described herein) onto an array (e.g., any of the exemplary arrays described herein), wherein the array has a plurality of first probes (e.g., any of the exemplary first probes described herein) affixed (i.e., attached) to the array. In some embodiments, the array is contacted with a biological sample and a plurality of second and third probes. In some embodiments, the array is contacted with the plurality of second and third probes prior to the placement of the biological sample.

In some embodiments of any of the methods described herein, the first probe, the second probe, and the third probe hybridize, assemble, and penetrate the biological sample.

In some embodiments of any of the methods described herein, the biological sample has not been treated with a permeabilization agent (e.g., any of the permeabilization agents described herein). In some embodiments, the biological sample that has not been treated with a permeabilization agent can be a fresh frozen tissue sample. In some embodiments, the biological sample has been treated with a permeabilization agent (e.g., one or more of any of the permeabilization agents described herein). In some embodiments of any of the methods described herein, the biological sample has been treated with a fixation agent (e.g., any of the fixation agents described herein).

In some embodiments of any of the methods described herein, the biological sample can be a tissue sample. In some examples of any of the methods described herein, the tissue sample can be a tissue section. For example, the biological sample can be a formalin-fixed paraffin-embedded tissue sample or a fresh frozen tissue sample. A biological sample could be a tissue sample from a plant. In some examples, a tissue sample is from a human, a non-human primate, mammals, non-mammalian eukaryotes, and the like. The present disclosure is not limited by the source of the tissue sample.

In some embodiments, the biological sample as described herein can be stained or imaged using any of the exemplary methods described herein.

In some embodiments of any of the methods described herein, the target analyte can be a protein or a nucleic acid. Non-limiting examples of a target nucleic acid include DNA analytes such as genomic DNA, methylated DNA, specific methylated DNA sequences, fragmented DNA, mitochondrial DNA, in situ synthesized PCR products, and RNA/DNA hybrids.

Non-limiting examples of the target nucleic acid also include RNA analytes such as various types of coding and non-coding RNA. Examples of the different types of RNA analytes include messenger RNA (mRNA), ribosomal RNA (rRNA), transfer RNA (tRNA), microRNA (miRNA), and viral RNA. The RNA can be a transcript (e.g. present in a tissue section). The RNA can be small (e.g., less than 200 nucleic acid bases in length) or large (e.g., RNA greater than 200 nucleic acid bases in length). Small RNAs mainly include 5.8S ribosomal RNA (rRNA), 5S rRNA, transfer RNA (tRNA), micro RNA (miRNA), small interfering RNA (siRNA), small nucleolar RNA (snoRNAs), Piwi-interacting RNA (piRNA), tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments, the target nucleic acid can include a mutation (e.g., a disease-causing mutation, e.g., a cancer-causing mutation). In some embodiments, the target nucleic acid includes single nucleotide polymorphism, a gene amplification, insertions, deletions, or a chromosomal translocation.

An analyte capture agent of the plurality of analyte capture agents comprises an analyte binding moiety barcode, an analyte capture sequence, and an analyte binding moiety (e.g., any of the analyte binding moieties described herein) that specifically binds to a target analyte (e.g., any of the target analytes described herein).

In some embodiments of any of the methods described herein, a probe containing an analyte capture domain can be extended using the target analyte specifically bound to the capture domain as a template.

The invention claimed is:

1. A composition, comprising:
   a nucleic acid array comprising a support having a plurality of first probes affixed to the support, wherein each of the first probes comprises 2, 3, 4, or 5 copies of a first nucleotide hybridization sequence; and
   a plurality of second probes, wherein each of the second probes comprises (i) a second hybridization sequence complementary to the first nucleotide hybridization sequence, and (ii) a unique molecular identifier;
   wherein:
   two or more of the copies of the first nucleotide hybridization sequence in each of the first probes are hybridized to the second nucleotide hybridization sequence of the second probes;
   each of the first probes and each of the second probes comprises a unique spatial barcode associated with a unique location on the nucleic acid array; and
   the unique spatial barcode of each of the first probes and each of the second probes does not substantially hybridize to a nucleic acid in a biological sample.

2. The composition of claim 1, wherein each of the second probes includes 2, 3, 4, or 5 copies of a third nucleotide hybridization sequence, and the composition additionally comprises:
   a plurality of third probes, wherein each of the third probes comprises a fourth nucleotide hybridization sequence complementary to the third nucleotide hybridization sequence;
   wherein two or more of the copies of the third nucleotide hybridization sequence in each of the second probes are hybridized to the fourth nucleotide hybridization sequence of the third probes.

3. The composition of claim 2, wherein a melting temperature for a duplex formed by hybridization of a copy of the first nucleotide hybridization sequence with a copy of the second nucleotide hybridization sequence is greater than a melting temperature for a duplex formed by hybridization of a copy of the third nucleotide hybridization sequence with a copy of the fourth nucleotide hybridization sequence.

4. The composition of claim 2, wherein each of the third probes comprises a unique spatial barcode associated with a unique location on the nucleic acid array.

5. The composition of claim 4, wherein each of the third probes further comprises a capture domain.

6. The composition of claim 5, wherein the capture domain comprises a poly(T) nucleotide sequence.

7. The composition of claim 5, wherein the capture domain is bound to an analyte from a biological sample.

8. The composition of claim 1, wherein each of the first probes comprises 2 copies of the first nucleotide hybridization sequence.

9. The composition of claim 8, wherein each of the second probes comprises 2 copies of the second nucleotide hybridization sequence.

10. The composition of claim 1, wherein each of the first probes further comprises a capture domain.

11. The composition of claim 10, wherein the capture domain comprises a poly(T) nucleotide sequence.

12. The composition of claim 10, wherein the capture domain is bound to an analyte from a biological sample.

13. The composition of claim 1, wherein each of the first probes further comprises a unique molecular identifier.

14. The composition of claim 1, wherein each of the second probes further comprises a capture domain.

15. The composition of claim 14, wherein the capture domain comprises a poly(T) nucleotide sequence.

16. The composition of claim 14, wherein the capture domain is bound to an analyte from a biological sample.

* * * * *